US009198851B2

(12) United States Patent
Plos et al.

(10) Patent No.: US 9,198,851 B2
(45) Date of Patent: Dec. 1, 2015

(54) COMPOSITION COMPRISING AT LEAST ONE SPECIFIC ALKOXYSILANE POLYMER

(71) Applicant: L'OREAL, Paris (FR)

(72) Inventors: Gregory Plos, Paris (FR); Anne Bouchara, Paris (FR); Patrice Lerda, Asnieres (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 14/373,674

(22) PCT Filed: Jan. 23, 2013

(86) PCT No.: PCT/EP2013/051232
§ 371 (c)(1),
(2) Date: Jul. 22, 2014

(87) PCT Pub. No.: WO2013/110653
PCT Pub. Date: Aug. 1, 2013

(65) Prior Publication Data
US 2015/0027482 A1 Jan. 29, 2015

Related U.S. Application Data

(60) Provisional application No. 61/604,754, filed on Feb. 29, 2012.

(30) Foreign Application Priority Data

Jan. 23, 2012 (FR) ...................... 12 50619

(51) Int. Cl.
A61Q 5/12 (2006.01)
A61K 8/86 (2006.01)
A61K 8/58 (2006.01)
A61Q 5/04 (2006.01)
A61Q 5/06 (2006.01)
A45D 7/06 (2006.01)
A61K 8/34 (2006.01)
A61K 8/365 (2006.01)
A61K 8/37 (2006.01)
A61K 8/41 (2006.01)
A61K 8/73 (2006.01)
A45D 7/00 (2006.01)

(52) U.S. Cl.
CPC ... *A61K 8/86* (2013.01); *A45D 7/06* (2013.01); *A61K 8/342* (2013.01); *A61K 8/365* (2013.01); *A61K 8/37* (2013.01); *A61K 8/416* (2013.01); *A61K 8/585* (2013.01); *A61K 8/737* (2013.01); *A61Q 5/04* (2013.01); *A61Q 5/06* (2013.01); *A61Q 5/12* (2013.01); *A45D 2007/002* (2013.01); *A61K 2800/24* (2013.01); *A61K 2800/884* (2013.01); *A61K 2800/95* (2013.01)

(58) Field of Classification Search
CPC ........... A61Q 5/06; A61Q 5/12; A61K 8/585; A61K 8/898; A45D 7/06; A45D 2007/002

USPC .................................................... 424/70.122
See application file for complete search history.

(56) References Cited

U.S. PATENT DOCUMENTS 2,261,002 A 10/1941 Ritter
2,271,378 A 1/1942 Searle
(Continued)

FOREIGN PATENT DOCUMENTS

CA 1069522 A1 1/1980
DE 4402929 C1 6/1995
(Continued)

OTHER PUBLICATIONS

STIC Search Report dated Dec. 15, 2014.*
(Continued)

Primary Examiner — Eisa Elhilo
(74) Attorney, Agent, or Firm — The Marbury Law Group, PLLC

(57) ABSTRACT

The present invention relates to a cosmetic composition comprising: —one or more keratin fiber conditioning agents; —one or more polymers of formula (I): in which: —$Z_1$ represents a divalent group —$CH_2$-T or -T-$CH_2$—; T denoting an oxygen or sulfur atom, or a group chosen from the groups $N(R_2)$, $N(R_2)$—C(O), C(O)—$N(R_2)$, S—(CO), (CO)—S, O—(CO) and (CO)—O; —$Z_2$ represents a group $OR_1$ or $R_8$—$CH_2$—$NR_3R_4$; —$Z_3$ represents a group $OR_5$ or $R_6$; —p1 is equal to 1; —p2 is equal to 0 or 1; —$R_2$ and $R_3$, which may be identical or different, represent a hydrogen atom or a group R7; $R_1$, $R_5$, $R_6$, $R_7$ and $R_8$, which may be identical or different, represent a $C_1$-$C_6$ and preferably $C_1$-$C_2$ alkyl group; and $R_4$ represents a $C_1$-$C_6$ and preferably $C_1$-$C_2$ alkyl group, or a $C_5$-$C_6$ and preferably $C_6$ cycloalkyl group such as cyclohexyl; $R_3$ and $R_4$ may optionally form, with the nitrogen atom that bears them, a 5- to 8-membered heterocycle comprising from 1 to 3 heteroatoms; —W represents a divalent polymer chain. The invention also relates to processes using this composition with or without catalysts and devices.

$$Z_2-\underset{\underset{Z_3}{|}}{\overset{\overset{O-R_1}{|}}{Si}}-(Z_1)_{p1}-(O)_{p2}-W-(O)_{p2}-(Z_1)_{p1}-\underset{\underset{Z_3}{|}}{\overset{\overset{R_1-O}{|}}{Si}}-Z_2 \quad (I)$$

20 Claims, No Drawings

(56) References Cited

U.S. PATENT DOCUMENTS

| | | |
|---|---|---|
| 2,273,780 A | 2/1942 | Dittmar |
| 2,375,853 A | 5/1945 | Kirby et al. |
| 2,388,614 A | 11/1945 | Kirby et al. |
| 2,454,547 A | 11/1948 | Bock et al. |
| 2,961,347 A | 11/1960 | Floyd |
| 3,206,462 A | 9/1965 | McCarty |
| 3,227,615 A | 1/1966 | Korden |
| 3,472,840 A | 10/1969 | Stone et al. |
| 3,589,978 A | 6/1971 | Kamal et al. |
| 3,632,559 A | 1/1972 | Matter et al. |
| 3,836,537 A | 9/1974 | Boerwinkle et al. |
| 3,910,862 A | 10/1975 | Barabas et al. |
| 3,912,808 A | 10/1975 | Sokol |
| 3,917,817 A | 11/1975 | Vanlerberghe et al. |
| 3,929,990 A | 12/1975 | Green et al. |
| 3,966,904 A | 6/1976 | Green et al. |
| 3,986,825 A | 10/1976 | Sokol |
| 4,001,432 A | 1/1977 | Green et al. |
| 4,005,193 A | 1/1977 | Green et al. |
| 4,013,787 A | 3/1977 | Varlerberghe et al. |
| 4,025,617 A | 5/1977 | Green et al. |
| 4,025,627 A | 5/1977 | Green et al. |
| 4,025,653 A | 5/1977 | Green et al. |
| 4,026,945 A | 5/1977 | Green et al. |
| 4,027,008 A | 5/1977 | Sokol |
| 4,027,020 A | 5/1977 | Green et al. |
| 4,031,307 A | 6/1977 | DeMartino et al. |
| 4,075,136 A | 2/1978 | Schaper |
| 4,131,576 A | 12/1978 | Iovine et al. |
| 4,137,180 A | 1/1979 | Naik et al. |
| 4,165,367 A | 8/1979 | Chakrabarti |
| 4,166,894 A | 9/1979 | Schaper |
| 4,172,887 A | 10/1979 | Vanlerberghe et al. |
| 4,189,468 A | 2/1980 | Vanlerberghe et al. |
| 4,197,865 A | 4/1980 | Jacquet et al. |
| 4,217,914 A | 8/1980 | Jacquet et al. |
| 4,223,009 A | 9/1980 | Chakrabarti |
| 4,240,450 A | 12/1980 | Grollier et al. |
| 4,277,581 A | 7/1981 | Vanlerberghe et al. |
| 4,348,202 A | 9/1982 | Grollier et al. |
| 4,349,532 A | 9/1982 | Vanlerberghe et al. |
| 4,381,919 A | 5/1983 | Jacquet et al. |
| 4,422,853 A | 12/1983 | Jacquet et al. |
| 4,445,521 A | 5/1984 | Grollier et al. |
| 4,579,732 A | 4/1986 | Grollier et al. |
| 4,591,610 A | 5/1986 | Grollier |
| 4,608,250 A | 8/1986 | Jacquet et al. |
| 4,693,935 A | 9/1987 | Mazurek |
| 4,719,099 A | 1/1988 | Grollier et al. |
| 4,728,571 A | 3/1988 | Clemens et al. |
| 4,761,273 A | 8/1988 | Grollier et al. |
| 4,777,040 A | 10/1988 | Grollier et al. |
| 4,778,823 A | 10/1988 | Kawamata et al. |
| 4,839,166 A | 6/1989 | Grollier et al. |
| 4,874,554 A | 10/1989 | Lange et al. |
| 4,948,579 A | 8/1990 | Jacquet et al. |
| 4,957,732 A | 9/1990 | Grollier et al. |
| 4,970,066 A | 11/1990 | Grollier et al. |
| 4,972,037 A | 11/1990 | Garbe et al. |
| 4,996,059 A | 2/1991 | Grollier et al. |
| 5,009,880 A | 4/1991 | Grollier et al. |
| 5,089,252 A | 2/1992 | Grollier et al. |
| 5,196,189 A | 3/1993 | Jacquet et al. |
| 5,525,709 A | 6/1996 | Davey et al. |
| 5,616,746 A | 4/1997 | Mahieu et al. |
| 5,618,523 A | 4/1997 | Zysman et al. |
| 5,773,611 A | 6/1998 | Zysman et al. |
| 5,958,392 A | 9/1999 | Grollier et al. |
| 6,001,376 A | 12/1999 | Mahieu et al. |
| 6,210,691 B1 | 4/2001 | Mahieu et al. |
| 7,319,128 B2 | 1/2008 | Ziche et al. |
| 2002/0146382 A1 | 10/2002 | Mallo et al. |
| 2007/0134191 A1 | 6/2007 | Singer |
| 2010/0179105 A1 | 7/2010 | Blin et al. |
| 2012/0174508 A1* | 7/2012 | Brooks et al. .................. 52/232 |
| 2012/0260934 A1 | 10/2012 | Schweinsberg et al. |

FOREIGN PATENT DOCUMENTS

| | | |
|---|---|---|
| DE | 4420736 C1 | 8/1995 |
| DE | 4424530 A1 | 1/1996 |
| DE | 4424533 A1 | 1/1996 |
| EP | 0080976 A1 | 6/1983 |
| EP | 0122324 A1 | 10/1984 |
| EP | 0186507 A2 | 7/1986 |
| EP | 0227994 A1 | 7/1987 |
| EP | 0337354 A1 | 10/1989 |
| EP | 0642834 A2 | 11/1989 |
| EP | 0412704 A2 | 2/1991 |
| EP | 0412707 A1 | 2/1991 |
| EP | 0582152 A2 | 2/1994 |
| EP | 0646572 A1 | 4/1995 |
| FR | 1400366 A | 5/1965 |
| FR | 1492597 A | 8/1967 |
| FR | 1583363 A | 10/1969 |
| FR | 2077143 A | 10/1971 |
| FR | 2080759 A | 11/1971 |
| FR | 2162025 A1 | 7/1973 |
| FR | 2190406 A2 | 2/1974 |
| FR | 2252840 A1 | 6/1975 |
| FR | 2270846 A1 | 12/1975 |
| FR | 2280361 A2 | 2/1976 |
| FR | 2316271 A1 | 1/1977 |
| FR | 2320330 A1 | 3/1977 |
| FR | 2336434 A1 | 7/1977 |
| FR | 2368508 A2 | 5/1978 |
| FR | 2383660 A1 | 10/1978 |
| FR | 2393573 A1 | 1/1979 |
| FR | 2413907 A1 | 8/1979 |
| FR | 2470596 A1 | 6/1981 |
| FR | 2505348 A1 | 11/1982 |
| FR | 2519863 A1 | 7/1983 |
| FR | 2542997 A1 | 9/1984 |
| FR | 2598476 A1 | 5/1987 |
| FR | 2598611 A1 | 11/1987 |
| FR | 2673179 A1 | 8/1992 |
| FR | 2916970 A1 | 12/2008 |
| GB | 1021400 A | 3/1966 |
| GB | 1331819 A | 9/1973 |
| GB | 1546809 A | 5/1979 |
| GB | 2407496 A | 5/2005 |
| WF | 9323009 A1 | 11/1993 |
| WO | 9323446 A2 | 11/1993 |
| WO | 9407844 A1 | 4/1994 |
| WO | 9410131 A1 | 5/1994 |
| WO | 9424097 A1 | 10/1994 |
| WO | 9500578 A1 | 1/1995 |
| WO | 9516665 A1 | 5/1995 |
| WO | 9523807 A1 | 9/1995 |
| WO | 2008148805 A2 | 12/2008 |
| WO | 2011080034 A2 | 7/2011 |

OTHER PUBLICATIONS

International Search Report for PCT/EP2013/051232, (2013).
English language Abstract for DE 4402929, (1995).
English language Abstract for DE 4420736, (1995).
English language Abstract for DE 4424530, (1996).
English language Abstract for DE 4424533, (1996).
English language Abstract for EP 0080976, (1996).
English language Abstract for FR 2589476, (1987).
Todd, Charles et al., "Volatile Silicone Fluids for Cosmetic Formulations", Cosmetics and Toiletries, vol. 91, Jan. 1976, pp. 29-32.

* cited by examiner

COMPOSITION COMPRISING AT LEAST ONE SPECIFIC ALKOXYSILANE POLYMER

This is a national stage of International Application No. PCT/EP2013/051232, filed on Jan. 23, 2013, which claims priority to U.S. Provisional Application No. 61/604,754, filed on Feb. 29, 2012, as well as French Application No. 1250619, filed on Jan. 23, 2012, all of which are incorporated herein by reference in their entireties.

The invention relates to a composition and a process for shaping the hair.

Two main categories of hair-shaping products are generally used: styling products and permanent-waving products.

Styling products allow non-permanent shaping of the hair. They are used on wet or dry hair before shaping by hand or using a brush or a comb. They are in the form of gels, mousses, waxes, pastes, lacquers or sprays. After applying them to the hair and after drying, these products harden substantially. This is reflected by an unnatural dry, corporified feel necessary for holding and volumizing the hairstyle. However, these styling products become eliminated on shampooing. They therefore need to be applied daily.

Permanent-waving products allow long-lasting shaping of the hair.

Generally, the technique used for permanently reshaping the hair consists, in a first stage, in opening the —S—S— disulfide bonds of keratin (cystine) by applying to the hair, which has been placed under tension beforehand (with curlers and other tensioning means), a reducing composition (reduction step) and then, preferably after having rinsed the head of hair thus treated, in reconstituting said disulfide bonds in a second stage by applying to the hair, which is still under tension, an oxidizing composition (oxidation step, also known as the fixing step) so as to finally give the hair the desired shape.

The new shape imposed on the hair by a chemical treatment such as that above is long-lasting and especially withstands the action of washing with water or with shampoo.

However, such a technique is not entirely satisfactory. Specifically, this technique is very efficient for modifying the shape of the hair, but causes substantial degradation of the hair fibres.

These two systems do not afford a sufficient cosmetic quality and/or durability of the effect obtained.

There is thus a need for a process that is fast and simple to use, which is not aggressive on the hair, and which makes it possible to obtain good shampoo-fast hairstyle hold, the hair having a satisfactory cosmetic quality, especially in terms of softness, sheen and absence of a tacky feel.

Document WO 2011/080 034 describes compositions comprising a macromolecule with an alkoxysilyl function and a trialkoxysilane for treating the hair, especially for temporarily reshaping keratin fibres, which show good resistance to washing. However, the cosmetic properties imparted to the hair are not entirely satisfactory.

Consequently, there is a need for hair compositions that can give the hair the desired shape in a long-lasting manner, while at the same time having very good cosmetic properties.

The aim of the present invention is, precisely, to satisfy these needs.

According to one of its aspects, the invention relates to a cosmetic composition comprising
one or more keratin fibre conditioning agents;
one or more polymers of formula (I) defined below.

The present invention also relates to a cosmetic process for treating keratin fibres such as the hair, which consists in applying thereto a composition as defined previously, and optionally in simultaneously or sequentially applying one or more catalysts chosen from organic or mineral basic compounds, especially ammonia, sodium hydroxide, organic or mineral acids, especially hydrochloric acid, oleic acid or lactic acid, and mixtures thereof, or an alkoxysilane monomer, especially aminopropyltriethoxysilane.

The present invention also relates to a multi-compartment device comprising:
a first compartment containing a composition as defined previously;
a second compartment containing one or more catalysts chosen from organic or mineral basic compounds, especially ammonia, sodium hydroxide, organic or mineral acids, especially hydrochloric acid, oleic acid and lactic acid, and mixtures thereof, or an alkoxysilane monomer, especially aminopropyltriethoxysilane.

Finally, the present invention relates to the use of the composition as defined previously for treating keratin fibres, especially the hair, and in particular for coating the hair.

The composition of the invention comprises one or more polymers of formula (I) below:

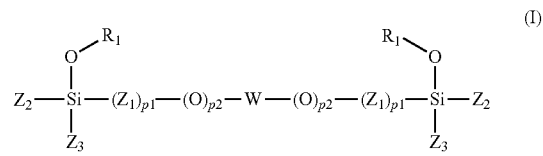

in which:
$Z_1$ represents a divalent group —$CH_2$-T- or -T-$CH_2$—; T denoting an oxygen or sulfur atom, or a group chosen from the groups N($R_2$), N($R_2$)—C(O), C(O)—N($R_2$), S—(CO), (CO)—S, O—(CO) and (CO)—O;
$Z_2$ represents a group $OR_1$ or $R_8$—$CH_2$—$NR_3R_4$;
$Z_3$ represents a group $OR_5$ or $R_6$;
p1 is equal to 1;
p2 is equal to 0 or 1;
$R_2$ and $R_3$, which may be identical or different, represent a hydrogen atom or a group $R_7$;
$R_1$, $R_5$, $R_6$, $R_7$ and $R_8$, which may be identical or different, represent a $C_1$-$C_6$ and preferably $C_1$-$C_2$ alkyl group;
and $R_4$ represents a $C_1$-$C_6$ and preferably $C_1$-$C_2$ alkyl group, or a $C_5$-$C_6$ and preferably $C_6$ cycloalkyl group such as cyclohexyl;
$R_3$ and $R_4$ may optionally form, with the nitrogen atom that bears them, a 5- to 8-membered heterocycle comprising from 1 to 3 heteroatoms;
W represents a divalent polymer chain.

The groups ($C_1$-$C_6$) are preferably methyl or ethyl groups.

The term "polymer" means a macromolecule formed from a repeating sequence of units originating from one or more monomers.

Preferably, the polymers of formula (I) comprise at least one group —$CH_2$—N($R_2$)—C(O)— or —C(O)—N($R_2$)—$CH_2$— or —$CH_2$—$NR_3R_4$. In one variant of the invention, the polymer chain W is a ($C_1$-$C_6$) polyoxyalkylene, especially of formula —(O-ALK)$_n$- ALK being a $C_1$-$C_6$ alkylene group, preferably ethylene, and n being between 5 and 100 000 and preferably between 20 and 100 000.

A polymer group described in U.S. Pat. No. 7,319,128 will be used, for example.

According to one particular embodiment, the polymer chain W is a polyether. As polymer of formula (I), use will be made, for example, of a polyether terminated with dimethoxy (methyl)silylmethyl carbamate groups sold by the company Wacker under the trade reference Geniosil STP-E10.

The content of the polymer(s) of formula (I) in the composition generally ranges from 0.1% to 40% by weight, preferably from 0.5% to 30% by weight and more particularly from 1% to 10% by weight relative to the total weight of the composition.

The composition according to the invention also comprises one or more conditioning agents.

In the context of the present patent application, the term "keratin fibre conditioning agent" means any agent whose function is to improve the cosmetic properties of the hair, in particular the softness, sheen, disentangling, feel, smoothness and static electricity.

The conditioning agents may be in liquid, semi-solid or solid form, for instance oils, waxes or gums.

According to the invention, the conditioning agents may be chosen from fatty substances such as $C_6$-$C_{16}$ hydrocarbons or hydrocarbons containing more than 16 carbon atoms and in particular alkanes, oils of animal origin, oils of plant origin, glycerides or fluoro oils of synthetic origin, fatty alcohols, fatty acid and/or fatty alcohol esters, non-silicone waxes, silicones, fatty amines, fatty acids, cationic polymers, amphoteric polymers, cationic proteins, cationic protein hydrolysates, compounds of ceramide type, cationic surfactants, and also mixtures of these various compounds.

It is recalled that, for the purposes of the invention, the fatty alcohols, fatty esters and fatty acids more particularly contain one or more linear or branched, saturated or unsaturated hydrocarbon-based groups containing 6 to 30 carbon atoms, which are optionally substituted, in particular with one or more hydroxyl groups (in particular 1 to 4). If they are unsaturated, these compounds may comprise one to three conjugated or unconjugated carbon-carbon double bonds.

As regards the $C_6$-$C_{16}$ alkanes, they are linear or branched, and optionally cyclic. Examples that may be mentioned include hexane, dodecane and isoparaffins such as isohexadecane and isodecane. The linear or branched hydrocarbons containing more than 16 carbon atoms may be chosen from liquid paraffins, petroleum jelly, liquid petroleum jelly, polydecenes, and hydrogenated polyisobutene such as Parleam®.

Among the animal oils, mention may be made of perhydrosqualene.

Among the triglycerides of plant or synthetic origin, mention may be made of liquid fatty acid triglycerides containing from 6 to 30 carbon atoms, for instance heptanoic or octanoic acid triglycerides, or alternatively, for example, sunflower oil, corn oil, soybean oil, marrow oil, grapeseed oil, sesame seed oil, hazelnut oil, apricot oil, macadamia oil, arara oil, sunflower oil, castor oil, avocado oil, jojoba oil, shea butter oil and caprylic/capric acid triglycerides, for instance those sold by the company Stearineries Dubois or those sold under the names Miglyol® 810, 812 and 818 by the company Dynamit Nobel.

Among the fluoro oils, mention may also be made of perfluoromethylcyclopentane and perfluoro-1,3-dimethylcyclohexane, sold under the names Flutec® PC1 and Flutec® PC3 by the company BNFL Fluorochemicals; perfluoro-1,2-dimethylcyclobutane; perfluoroalkanes such as dodecafluoropentane and tetradecafluorohexane, sold under the names PF 5050® and PF 5060® by the company 3M, or bromoperfluorooctyl sold under the name Foralkyl® by the company Atochem; nonafluoromethoxybutane and nonafluoroethoxyisobutane; perfluoromorpholine derivatives such as 4-trifluoromethyl perfluoromorpholine sold under the name PF 5052® by the company 3M.

The fatty alcohols that may be used in the cosmetic composition are saturated or unsaturated, and linear or branched, and comprise from 6 to 30 carbon atoms and more particularly from 8 to 30 carbon atoms. Mention may be made, for example, of cetyl alcohol, stearyl alcohol and their mixture (cetearyl alcohol), octyldodecanol, 2-butyloctanol, 2-hexyldecanol, 2-undecylpentadecanol, oleyl alcohol or linoleyl alcohol.

The wax(es) that may be used in the cosmetic composition are chosen especially from carnauba wax, candelilla wax, esparto grass wax, paraffin wax, ozokerite, plant waxes, for instance olive wax, rice wax, hydrogenated jojoba wax or the absolute waxes of flowers such as the essential wax of blackcurrant blossom sold by Bertin (France), animal waxes, for instance beeswaxes, or modified beeswaxes (cerabellina); other waxes or waxy starting materials that may be used according to the invention are especially marine waxes such as the product sold by Sophim as M82, and polyethylene waxes or polyolefin waxes in general.

As regards the esters of fatty acids and/or of fatty alcohols, advantageously different from the triglycerides mentioned above, mention may be made especially of esters of saturated or unsaturated, linear or branched $C_1$-$C_{26}$ aliphatic mono- or polyacids and of saturated or unsaturated, linear or branched $C_1$-$C_{26}$ aliphatic mono- or polyalcohols, the total carbon number of the esters more particularly being greater than or equal to 10.

Among the monoesters, mention may be made of dihydroabietyl behenate; octyldodecyl behenate; isocetyl behenate; cetyl lactate; $C_{12}$-$C_{15}$ alkyl lactate; isostearyl lactate; lauryl lactate; linoleyl lactate; oleyl lactate; (iso)stearyl octanoate; isocetyl octanoate; octyl octanoate; cetyl octanoate; decyl oleate; isocetyl isostearate; isocetyl laurate; isocetyl stearate; isodecyl octanoate; isodecyl oleate; isononyl isononanoate; isostearyl palmitate; methylacetyl ricinoleate; myristyl stearate; octyl isononanoate; 2-ethylhexyl isononanoate; octyl palmitate; octyl pelargonate; octyl stearate; octyldodecyl erucate; oleyl erucate; ethyl and isopropyl palmitates, 2-ethylhexyl palmitate, 2-octyldecyl palmitate, alkyl myristates such as isopropyl, butyl, cetyl, 2-octyldodecyl, myristyl or stearyl myristate, hexyl stearate, butyl stearate, isobutyl stearate; dioctyl malate, hexyl laurate, 2-hexyldecyl laurate.

Still within the context of this variant, it is also possible to use esters of $C_4$-$C_{22}$ dicarboxylic or tricarboxylic acids and of $C_1$-$C_{22}$ alcohols, and esters of monocarboxylic, dicarboxylic or tricarboxylic acids and of $C_2$-$C_{26}$ di-, tri-, tetra- or pentahydroxy alcohols.

Mention may in particular be made of: diethyl sebacate; diisopropyl sebacate; diisopropyl adipate; di(n-propyl) adipate; dioctyl adipate; diisostearyl adipate; dioctyl maleate; glyceryl undecylenate; octyldodecyl stearoyl stearate; pentaerythrityl monoricinoleate; pentaerythrityl tetraisononanoate; pentaerythrityl tetrapelargonate; pentaerythrityl tetraisostearate; pentaerythrityl tetraoctanoate; propylene glycol dicaprylate; propylene glycol dicaprate; tridecyl erucate; triisopropyl citrate; triisostearyl citrate; glyceryl trilactate; glyceryl trioctanoate; trioctyldodecyl citrate; trioleyl citrate; propylene glycol dioctanoate; neopentyl glycol diheptanoate; diethylene glycol diisononanoate; and polyethylene glycol distearates.

Among the esters mentioned above, use is preferably made of ethyl, isopropyl, myristyl, cetyl or stearyl palmitate, 2-ethylhexyl palmitate, 2-octyldecyl palmitate, alkyl myristates, such as isopropyl, butyl, cetyl or 2-octyldodecyl myristate, hexyl stearate, butyl stearate, isobutyl stearate, dioctyl malate, hexyl laurate, 2-hexyldecyl laurate, isononyl isononanoate or cetyl octanoate.

The composition may also comprise, as fatty ester, sugar esters and diesters of $C_6$-$C_{30}$ and preferably $C_{12}$-$C_{22}$ fatty acids. It is recalled that the term "sugar" means oxygen-bearing hydrocarbon-based compounds containing several alcohol functions, with or without aldehyde or ketone functions, and which comprise at least 4 carbon atoms. These sugars can be monosaccharides, oligosaccharides or polysaccharides.

Mention may be made, as suitable sugars, for example, of sucrose (or saccharose), glucose, galactose, ribose, fucose, maltose, fructose, mannose, arabinose, xylose, lactose and their derivatives, in particular alkyl derivatives, such as methyl derivatives, for example methylglucose.

The sugar esters of fatty acids may be selected especially from the group comprising the esters or mixtures of esters of sugars described previously and of linear or branched, saturated or unsaturated $C_6$-$C_{30}$ and preferably $C_{12}$-$C_{22}$ fatty acids. If they are unsaturated, these compounds may comprise from one to three conjugated or unconjugated carbon-carbon double bonds.

The esters according to this alternative form may also be chosen from mono-, di-, tri- and tetraesters, polyesters, and mixtures thereof.

These esters can, for example, be oleates, laurates, palmitates, myristates, behenates, cocoates, stearates, linoleates, linolenates, caprates, arachidonates or their mixtures, such as, in particular, oleate/palmitate, oleate/stearate or palmitate/stearate mixed esters.

More particularly, use is made of mono- and diesters and in particular mono- or di-oleate, -stearate, -behenate, -oleate/palmitate, -linoleate, -linolenate or -oleate/stearate of sucrose, glucose or methylglucose.

An example that may be mentioned is the product sold under the name Glucate® DO by the company Amerchol, which is a methylglucose dioleate.

Examples of esters or mixtures of esters of sugar and of fatty acid that may also be mentioned include:
the products sold under the names F160, F140, F110, F90, F70 and SL40 by the company Crodesta, respectively denoting sucrose palmitostearates formed from 73% monoester and 27% diester and triester, from 61% monoester and 39% diester, triester and tetraester, from 52% monoester and 48% diester, triester and tetraester, from 45% monoester and 55% diester, triester and tetraester, from 39% monoester and 61% diester, triester and tetraester, and sucrose monolaurate;
the products sold under the name Ryoto Sugar Esters, for example referenced B370 and corresponding to sucrose behenate formed of 20% monoester and 80% diester, triester and polyester;
the sucrose monopalmitate/stearate-dipalmitate/stearate sold by Goldschmidt under the name Tegosoft® PSE.

The fatty acids are more particularly chosen from myristic acid, palmitic acid, stearic acid, behenic acid, oleic acid, linoleic acid, linolenic acid and isostearic acid.

The cationic polymers that may be used in accordance with the present invention may be chosen from any of those already known per se as improving the cosmetic properties of hair, namely, especially, those described in patent application EP-A-0 337 354 and in French patent applications FR-A-2 270 846, 2 383 660, 2 598 611, 2 470 596 and 2 519 863.

Even more generally, for the purposes of the present invention, the term "cationic polymer" denotes any polymer containing cationic groups and/or groups that can be ionized into cationic groups.

The preferred cationic polymers are chosen from those that contain units comprising primary, secondary, tertiary and/or quaternary amine groups that may either form part of the main polymer chain or may be borne by a side substituent directly connected thereto.

The cationic polymers used generally have a number-average or weight-average molar mass of between 500 and $5 \times 10^6$ approximately and preferably between $10^3$ and $3 \times 10^6$ approximately.

Among the cationic polymers that may be mentioned more particularly are polymers of the polyamine, polyaminoamide and polyquaternary ammonium type. These are known products.

The polymers of polyamine, polyamidoamide and polyquaternary ammonium type, that can be used in accordance with the present invention, and that can in particular be mentioned, are those described in French patents No. 2 505 348 or 2 542 997. Among these polymers, mention may be made of:

(1) homopolymers or copolymers derived from acrylic or methacrylic esters or amides and comprising at least one of the units of the following formulae:

$$\begin{array}{cc}
\text{—CH}_2\text{—C(R}_3\text{)—} & \text{—CH}_2\text{—C(R}_3\text{)—} \\
| & | \\
\text{O=C} & \text{O=C} \\
| & | \\
\text{O} & \text{O} \quad X^- \\
| & | \\
\text{A} & \text{A} \\
| & | \\
\text{N(R}_2\text{)(R}_1\text{)}, & \text{R}_4\text{—N}^+\text{—R}_6 \\
 & | \\
 & \text{R}_5
\end{array}$$

$$\begin{array}{cc}
\text{—CH}_2\text{—C(R}_3\text{)—} & \text{—CH}_2\text{—C(R}_3\text{)—} \\
| & | \\
\text{O=C} & \text{O=C} \\
| & | \\
\text{NH} & \text{NH} \quad X^- \\
| & | \\
\text{A} & \text{A} \\
| & | \\
\text{N(R}_1\text{)(R}_2\text{)} & \text{R}_4\text{—N}^+\text{—R}_6 \\
 & | \\
 & \text{R}_5
\end{array}$$

in which:

$R_3$, which may be identical or different, denote a hydrogen atom or a $CH_3$ radical;

A, which may be identical or different, represent a linear or branched alkyl group of 1 to 6 carbon atoms, preferably 2 or 3 carbon atoms, or a hydroxyalkyl group of 1 to 4 carbon atoms;

$R_4$, $R_5$ and $R_6$, which may be identical or different, represent an alkyl group containing from 1 to 18 carbon atoms or a benzyl radical, and preferably an alkyl group containing from 1 to 6 carbon atoms;

$R_1$ and $R_2$, which may be identical or different, represent hydrogen or an alkyl group containing from 1 to 6 carbon atoms and preferably methyl or ethyl;

X denotes an anion derived from a mineral or organic acid, such as a methosulfate anion or a halide such as chloride or bromide.

The copolymers of family (1) can also contain one or more units derived from comonomers that may be selected from the family of acrylamides, methacrylamides, diacetone acrylamides, acrylamides and methacrylamides substituted on the nitrogen with lower ($C_1$-$C_4$) alkyls, acrylic or methacrylic acids or esters thereof, vinyllactams such as vinylpyrrolidone or vinylcaprolactam, and vinyl esters.

Thus, among these copolymers of family (1), mention may be made of:

copolymers of acrylamide and of dimethylaminoethyl methacrylate quaternized with dimethyl sulfate or with a dimethyl halide, such as the product sold under the name Hercofloc by the company Hercules, copolymers of acrylamide and of methacryloyloxyethyltrimethylammonium chloride, described, for example, in patent application EP-A-080 976 and sold under the name Bina Quat P 100 by the company Ciba Geigy, the copolymers of acrylamide and of methacryloyloxyethyltrimethylammonium methosulfate sold under the name Reten by the company Hercules, quaternized or non-quaternized vinylpyrrolidone/dialkylaminoalkyl acrylate or methacrylate copolymers. These polymers are described in detail in French patents 2 077 143 and 2 393 573, dimethylaminoethyl methacrylate/vinylcaprolactam/vinylpyrrolidone terpolymers, vinylpyrrolidone/methacrylamidopropyldimethylamine copolymers, and quaternized vinylpyrrolidone/dimethylaminopropylmethacrylamide copolymers;

(2) cationic polysaccharides, especially cationic celluloses and galactomannan gums. Among the cationic polysaccharides, mention may be made more particularly of cellulose ether derivatives comprising quaternary ammonium groups, cationic cellulose copolymers or cellulose derivatives grafted with a water-soluble quaternary ammonium monomer and cationic galactomannan gums.

The cellulose ether derivatives comprising quaternary ammonium groups are described in French patent 1 492 597. These polymers are also defined in the CTFA dictionary as quaternary ammoniums of hydroxyethyl cellulose that have reacted with an epoxide substituted with a trimethylammonium group.

Cationic cellulose copolymers or cellulose derivatives grafted with a water-soluble monomer of quaternary ammonium are described especially in U.S. Pat. No. 4,131,576, such as hydroxyalkyl celluloses, for instance hydroxymethyl-, hydroxyethyl- or hydroxypropylcelluloses grafted, in particular, with a methacryloylethyltrimethylammonium, methacrylamidopropyltrimethylammonium or dimethyldiallylammonium salt.

The cationic galactomannan gums are described more particularly in U.S. Pat. Nos. 3,589,978 and 4,031,307, in particular guar gums containing cationic trialkylammonium groups. Guar gums modified by a 2,3-epoxypropyltrimethylammonium salt (e.g. chloride) are used, for example.

(3) polymers consisting of piperazinyl units and of divalent alkylene or hydroxyalkylene radicals containing straight or branched chains, optionally interrupted by oxygen, sulfur or nitrogen atoms or by aromatic or heterocyclic rings, and also the oxidation and/or quaternization products of these polymers. Such polymers are especially described in French patents 2 162 025 and 2 280 361;

(4) water-soluble polyaminoamides prepared in particular by polycondensation of an acidic compound with a polyamine; these polyaminoamides can be crosslinked with an epihalohydrin, a diepoxide, a dianhydride, an unsaturated dianhydride, a bisunsaturated derivative, a bis-halohydrin, a bisazetidinium, a bis-haloacyldiamine, a bis-alkyl halide or alternatively with an oligomer resulting from the reaction of a difunctional compound which is reactive with a bis-halohydrin, a bis-azetidinium, a bis-haloacyldiamine, a bis-alkyl halide, an epihalohydrin, a diepoxide or a bis-unsaturated derivative; the crosslinking agent being used in proportions ranging from 0.025 to 0.35 mol per amine group of the polyaminoamide; these polyaminoamides can be alkylated or, if they comprise one or more tertiary amine functions, they can be quaternized. Such polymers are especially described in French patents 2 252 840 and 2 368 508;

(5) polyaminoamide derivatives resulting from the condensation of polyalkylene polyamines with polycarboxylic acids followed by alkylation with difunctional agents. Mention may be made, for example, of adipic acid/dialkylaminohydroxyalkyldialkylenetriamine polymers in which the alkyl radical comprises from 1 to 4 carbon atoms and preferably denotes methyl, ethyl or propyl. Such polymers are especially described in French patent 1 583 363.

Among these derivatives, mention may be made more particularly of the adipic acid/dimethylaminohydroxypropyl/diethylenetriamine polymers sold under the name Cartaretine F, F4 or F8 by the company Sandoz.

(6) polymers obtained by reaction of a polyalkylene polyamine containing two primary amine groups and at least one secondary amine group with a dicarboxylic acid chosen from diglycolic acid and saturated aliphatic dicarboxylic acids having from 3 to 8 carbon atoms. The mole ratio of the polyalkylenepolyamine to the dicarboxylic acid being between 0.8:1 and 1.4:1, the polyaminoamide resulting therefrom is reacted with epichlorohydrin in a mole ratio of epichlorohydrin relative to the secondary amine group of the polyaminoamide of between 0.5:1 and 1.8:1. Such polymers are especially described in U.S. Pat. Nos. 3,227,615 and 2,961,347.

Polymers of this type are sold in particular under the name Hercosett 57 by the company Hercules Inc. or alternatively under the name PD 170 or Delsette 101 by the company Hercules in the case of the adipic acid/epoxypropyl/diethylenetriamine copolymer.

(7) co-cyclopolymers of alkyldiallylamine or of dialkyldiallylammonium, such as copolymers containing, as main constituent of the chain, units corresponding to formula (II) or (II'):

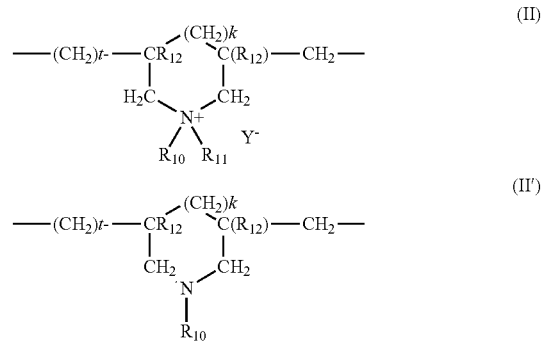

in which formulae k and t are equal to 0 or 1, the sum k+t being equal to 1; R12 denotes a hydrogen atom or a methyl radical; R10 and R11, independently of each other, denote an alkyl group having from 1 to 6 carbon atoms, a hydroxyalkyl group in which the alkyl group has preferably 1 to 5 carbon atoms, a lower ($C_1$-$C_4$) amidoalkyl group, or R10 and R11 may denote, together with the nitrogen atom to which they are attached, heterocyclic groups, such as piperidyl or morpholinyl; Y⁻ is an anion such as bromide, chloride, acetate, borate, citrate, tartrate, bisulfate, bisulfite, sulfate or phosphate. These polymers are especially described in French patent 2 080 759 and in its Certificate of Addition 2 190 406.

R10 and R11, independently of each other, preferably denote an alkyl group containing from 1 to 4 carbon atoms.

Among the polymers defined above, mention may be made more particularly of the copolymers of diallyldimethylammonium chloride and of acrylamide sold under the name Merquat 550 by the company Nalco.

(8) quaternary diammonium polymers containing repeating units corresponding to the formula:

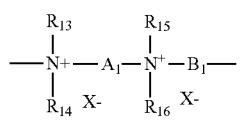

(III)

in which formula (III):

R13, R14, R15 and R16, which may be identical or different, represent aliphatic, alicyclic or arylaliphatic radicals containing from 1 to 20 carbon atoms, or lower hydroxyalkylaliphatic radicals, or else R13, R14, R15 and R16, together or separately, constitute, with the nitrogen atoms to which they are attached, heterocycles optionally containing a second heteroatom other than the nitrogen, or else R13, R14, R15 and R16 represent a linear or branched $C_1$-$C_6$ alkyl radical which is substituted by a nitrile, ester, acyl, amide or —CO—O—R17-D or —CO—NH—R17-D group in which R17 is an alkylene and D is a quaternary ammonium group;

A1 and B1 represent polymethylene groups containing from 2 to 20 carbon atoms, which may be linear or branched and saturated or unsaturated and may contain, bonded to or intercalated in the main chain, one or more aromatic rings, or one or more oxygen or sulfur atoms, or sulfoxide, sulfone, disulfide, amino, alkylamino, hydroxyl, quaternary ammonium, ureido, amide or ester groups, and X⁻ denotes an anion derived from a mineral or organic acid;

A1, R13 and R15 may form, with the two nitrogen atoms to which they are attached, a piperazine ring; moreover, if A1 denotes a saturated or unsaturated, linear or branched alkylene or hydroxyalkylene radical, B1 may also denote a group $(CH_2)_n$—CO-D-OC—$(CH_2)_n$— in which D denotes:

a) a glycol residue of formula: —O—Z—O—, where Z denotes a linear or branched hydrocarbon-based radical or a group corresponding to one of the following formulae:

—(CH2-CH2-O)x-CH2-CH2-

—[CH2-CH(CH3)-O]y-CH2-CH(CH3)- where x and y denote an integer from 1 to 4, representing a defined and unique degree of polymerization, or any number from 1 to 4, representing an average degree of polymerization;

b) a bis-secondary diamine residue such as a piperazine derivative;

c) a bis-primary diamine residue of formula: —NH—Y—NH—, where Y denotes a linear or branched hydrocarbon radical, or alternatively the divalent radical

—CH2-CH2-S—S—CH2-CH2-;

d) a ureylene group of formula: —NH—CO—NH—.

Preferably, X⁻ is an anion such as chloride or bromide.

These polymers have a number-average molecular mass generally of between 1000 and 100 000.

Polymers of this type are described in particular in French patents 2 320 330, 2 270 846, 2 316 271, 2 336 434 and 2 413 907 and U.S. Pat. Nos. 2,273,780, 2,375,853, 2,388,614, 2,454,547, 3,206,462, 2,261,002, 2,271,378, 3,874,870, 4,001,432, 3,929,990, 3,966,904, 4,005,193, 4,025,617, 4,025,627, 4,025,653, 4,026,945 and 4,027,020.

Use may be made more particularly of polymers that are composed of repeating units corresponding to the formula:

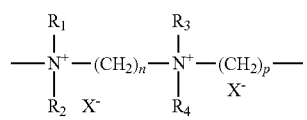

(a)

in which R1, R2, R3 and R4, which may be identical or different, denote an alkyl or hydroxyalkyl radical containing from 1 to 4 carbon atoms approximately, n and p are integers ranging from 2 to 20 approximately, and X⁻ is an anion derived from an organic or mineral acid.

One particularly preferred compound of formula (a) is that for which R1, R2, R3 and R4 represent a methyl radical and n=3, p=6 and X=Cl, which is called Hexadimethrine chloride according to the IN-CTFA) nomenclature.

(9) polyquaternary ammonium polymers comprising units of formula (IV):

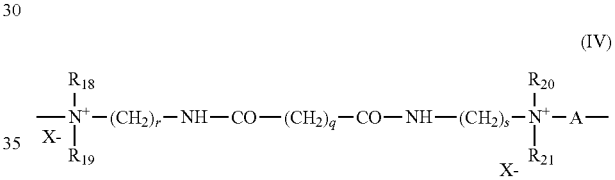

(IV)

in which formula:

R18, R19, R20 and R21, which may be identical or different, represent a hydrogen atom or a methyl, ethyl, propyl, β-hydroxyethyl, β-hydroxypropyl or —CH₂CH₂(OCH₂CH₂)pOH radical, in which p is equal to 0 or to an integer between 1 and 6, with the proviso that R18, R19, R20 and R21 do not simultaneously represent a hydrogen atom, r and s, which may be identical or different, are integers between 1 and 6, q is equal to 0 or to an integer between 1 and 34, X⁻ denotes an anion such as a halide, A denotes a radical of a dihalide or represents preferably —CH₂—CH₂—O—CH₂—CH₂—.

Such compounds are described especially in patent application EP-A-122 324.

Among these, mention may be made, for example, of the products Mirapol® A 15, Mirapol® AD1, Mirapol® A Z1 and Mirapol® 175, sold by the company Miranol;

(10) quaternary polymers of vinylpyrrolidone and of vinylimidazole, for instance the products sold under the names Luviquat® FC 905, FC 550 and FC 370 by the company BASF.

(11) crosslinked polymers of methacryloyloxy($C_1$-$C_4$) alkyltri($C_1$-$C_4$)alkylammonium salts, such as the polymers obtained by homopolymerization of dimethylaminoethyl methacrylate quaternized with methyl chloride, or by copolymerization of acrylamide with dimethylaminoethyl methacrylate quaternized with methyl chloride, the homopolymerization or copolymerization being followed by crosslinking with an olefinically unsaturated compound, more particularly methylenebisacrylamide.

Other cationic polymers that may be used in the context of the invention are polyalkyleneimines, in particular polyethyleneimines, polymers containing vinylpyridine or vinylpyridinium units, condensates of polyamines and of epichlorohydrin, polyquaternary ureylenes and chitin derivatives, especially chitosans or salts thereof; the salts that may be used are, in particular, chitosan acetate, lactate, glutamate, gluconate or pyrrolidonecarboxylate.

Among these compounds, mention may be made of chitosan having a degree of deacetylation of 90% by weight, chitosan pyrrolidonecarboxylate sold under the name Kytamer® PC by the company Amerchol.

Among all the cationic polymers that may be used in the context of the present invention, it is preferable to employ cationic cyclopolymers, in particular the dimethyldiallylammonium chloride homopolymers or copolymers sold under the names Merquat 100, Merquat 550 and Merquat S by the company Nalco, quaternary polymers of vinylpyrrolidone and of vinylimidazole, crosslinked homopolymers or copolymers of methacryloyloxy($C_1$-$C_4$)alkyltri($C_1$-$C_4$)alkylammonium salts, the chitosan pyrrolidonecarboxylate sold under the name Kytamer® PC by the company Amerchol, and mixtures thereof.

The amphoteric polymers that can be used in accordance with the present invention may be chosen from polymers comprising units K and M distributed randomly in the polymer chain, where K denotes a unit derived from a monomer comprising at least one basic nitrogen atom and M denotes a unit derived from an acid monomer comprising one or more carboxylic or sulfonic groups, or alternatively K and M can denote groups derived from carboxybetaine or sulfobetaine zwitterionic monomers; K and M can also denote a cationic polymer chain comprising primary, secondary, tertiary or quaternary amine groups, in which at least one of the amine groups carries a carboxylic or sulfonic group connected via a hydrocarbon-based radical, or alternatively K and M form part of a chain of a polymer comprising an α,β-dicarboxylic ethylene unit in which one of the carboxylic groups has been made to react with a polyamine comprising one or more primary or secondary amine groups.

The amphoteric polymers corresponding to the definition given above that are more particularly preferred are chosen from the following polymers:

(1) polymers resulting from the copolymerization of a monomer derived from a vinyl compound bearing a carboxylic group such as, more particularly, acrylic acid, methacrylic acid, maleic acid, α-chloroacrylic acid, and a basic monomer derived from a substituted vinyl compound containing at least one basic atom, such as, more particularly, dialkylaminoalkyl methacrylates and acrylates, and dialkylaminoalkylmethacrylamides and -acrylamides. Such compounds are described in U.S. Pat. No. 3,836,537. Mention may also be made of the sodium acrylate/acrylamidopropyltrimethylammonium chloride copolymer sold under the name Polyquart KE 3033 by the company Cognis.

The vinyl compound may also be a dialkyldiallylammonium salt such as the dimethyldiallylammonium salt (for example chloride). Copolymers of acrylic acid and of the latter monomer are sold under the names Merquat 280 and Merquat 295 by the company Nalco.

(2) Polymers comprising units deriving from:
a) at least one monomer chosen from acrylamides and methacrylamides substituted on the nitrogen with an alkyl radical, b) at least one acidic comonomer containing one or more reactive carboxylic groups, and c) at least one basic comonomer such as esters containing primary, secondary, tertiary and quaternary amine substituents of acrylic and methacrylic acids and the product of quaternization of dimethylaminoethyl methacrylate with dimethyl or diethyl sulfate.

The N-substituted acrylamides or methacrylamides that are more particularly preferred according to the invention are compounds in which the alkyl radicals contain from 2 to 12 carbon atoms and more particularly N-ethylacrylamide, N-tert-butylacrylamide, N-tert-octylacrylamide, N-octylacrylamide, N-decylacrylamide, N-dodecylacrylamide and the corresponding methacrylamides.

The acidic comonomers are chosen more particularly from acrylic acid, methacrylic acid, crotonic acid, itaconic acid, maleic acid and fumaric acid and alkyl monoesters, having 1 to 4 carbon atoms, or maleic or fumaric acids or anhydrides.

The preferred basic comonomers are aminoethyl, butylaminoethyl, N,N'-dimethylaminoethyl and N-tert-butylaminoethyl methacrylates.

Use is made more particularly of the copolymers whose CTFA (4th edition, 1991) name is octylacrylamide/acrylates/butylaminoethyl methacrylate copolymer.

(3) Crosslinked and alkylated polyaminoamides partially or totally deriving from polyaminoamides of general formula:

$$\mathrm{+CO-R_4-CO-Z+} \qquad (V)$$

in which R4 represents a divalent radical derived from a saturated dicarboxylic acid, a mono- or dicarboxylic aliphatic acid containing an ethylenic double bond, an ester of a lower alkanol having 1 to 6 carbon atoms of these acids, or a radical derived from the addition of any one of said acids to a bis (primary) or bis(secondary) amine, and Z denotes a radical derived from a bis(primary), mono- or bis(secondary) polyalkylene-polyamine and preferably represents:

a) in proportions of from 60 to 100 mol %, the radical

$$\mathrm{-NH+(CH_2)_x-NH+_p} \qquad (VI)$$

where x=2 and p=2 or 3, or alternatively x=3 and p=2
this radical being derived from diethylenetriamine, from triethylenetetramine or from dipropylenetriamine;

b) in proportions of from 0 to 40 mol %, the radical (VI) above in which x=2 and p=1 and which is derived from ethylenediamine, or the radical derived from piperazine:

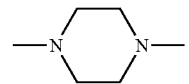

c) in proportions of from 0 to 20 mol %, the radical —NH(CH$_2$)$_6$—NH— being derived from hexamethylenediamine, these polyamino amines being crosslinked by addition reaction of a difunctional crosslinking agent chosen from epihalohydrins, diepoxides, dianhydrides and bis-unsaturated derivatives, using from 0.025 to 0.35 mol of crosslinking agent per amine group of the polyamino amide and alkylated by the action of acrylic acid, chloroacetic acid or an alkane sultone, or salts thereof.

The saturated carboxylic acids are preferably chosen from acids containing 6 to 10 carbon atoms, such as adipic acid, 2,2,4-trimethyladipic acid and 2,4,4-trimethyladipic acid, terephthalic acid, and acids containing an ethylenic double bond, for instance acrylic acid, methacrylic acid and itaconic acid.

The alkane sultones used in the alkylation are preferably propane sultone or butane sultone, the salts of the alkylating agents are preferably the sodium or potassium salts.

(4) Polymers comprising zwitterionic units of formula:

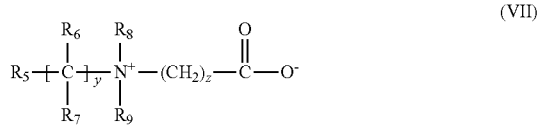

(VII)

in which R5 denotes a polymerizable unsaturated group such as an acrylate, methacrylate, acrylamide or methacrylamide group, y and z represent an integer from 1 to 3, R6 and R7 represent a hydrogen atom, or a methyl, ethyl or propyl group, R8 and R9 represent a hydrogen atom or an alkyl radical such that the sum of the carbon atoms in R8 and R9 does not exceed 10.

The polymers comprising such units may also comprise units derived from non-zwitterionic monomers such as dimethyl- or diethylaminoethyl acrylate or methacrylate or alkyl acrylates or methacrylates, acrylamides or methacrylamides or vinyl acetate.

An example that may be mentioned is the butyl methacrylate/dimethylcarboxymethylammonioethyl methacrylate copolymer.

(5) Polymers derived from chitosan comprising monomer units corresponding to formulae (VIII), (IX) and (X) below:

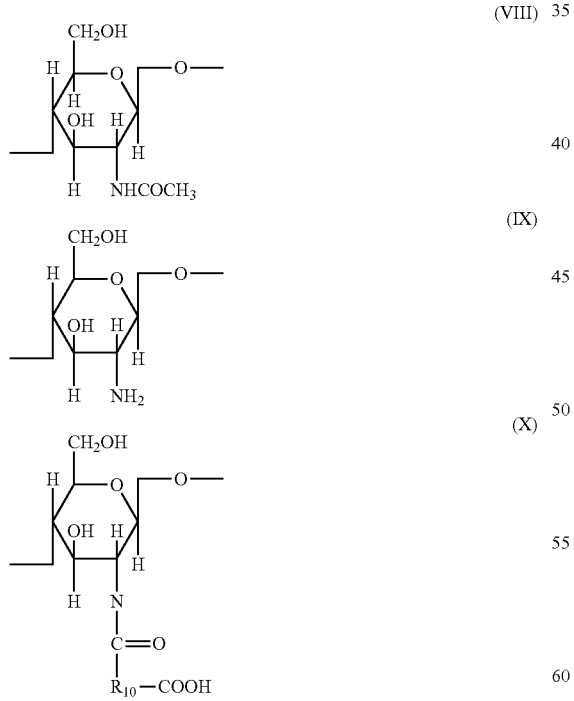

the unit (VIII) being present in proportions of between 0 and 30%, the unit (IX) in proportions of between 5% and 50% and the unit (X) in proportions of between 30% and 90%, it being understood that, in this unit (X), $R_{10}$ represents a radical of formula:

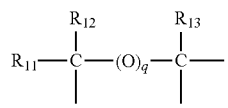

in which:

if q=0, R11, R12 and R13, which may be identical or different, each represent a hydrogen atom, a methyl, hydroxyl, acetoxy or amino residue, a monoalkylamine residue or a dialkylamine residue that are optionally interspersed with one or more nitrogen atoms and/or optionally substituted with one or more amine, hydroxyl, carboxyl, alkylthio or sulfonic groups, or an alkylthio residue in which the alkyl group bears an amino residue, at least one of the radicals R11, R12 and R13 being, in this case, a hydrogen atom;

or, if q=1, R11, R12 and R13 each represent a hydrogen atom, and also the salts formed by these compounds with bases or acids.

(6) Polymers derived from the N-carboxyalkylation of chitosan, such as N-carboxymethyl chitosan or N-carboxybutyl chitosan.

(7) Polymers corresponding to the general formula (XI) as described, for example, in French patent 1 400 366:

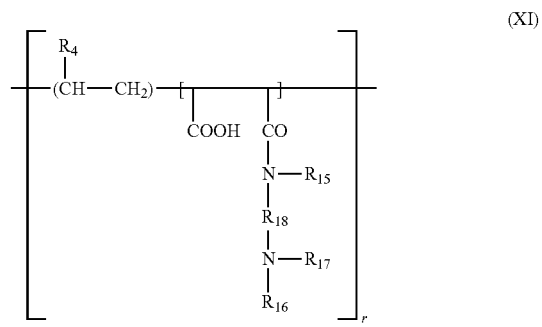

(XI)

in which R14 represents a hydrogen atom, a $CH_3O$, $CH_3CH_2O$ or phenyl radical, R15 denotes a hydrogen atom or a lower alkyl radical such as methyl or ethyl, R16 denotes a hydrogen atom or a lower alkyl radical such as methyl or ethyl, R17 denotes a lower alkyl radical such as methyl or ethyl or a radical corresponding to the formula: —R18-N(R16)$_2$, R18 representing a group —$CH_2$—$CH_2$—, —$CH_2$—$CH_2$—$CH_2$— or —$CH_2$—$CH(CH_3)$—, R16 having the meanings mentioned above, and also the higher homologues of these radicals, containing up to 6 carbon atoms.

(8) amphoteric polymers of the type -D-X-D-X— chosen from:

a) polymers obtained by the action of chloroacetic acid or sodium chloroacetate on compounds comprising at least one unit of formula:

-D-X-D-X-D- (XII)

where D denotes a radical

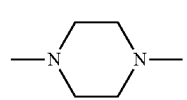

and X denotes the symbol E or E', E or E', which may be identical or different, denote a divalent radical that is an alkylene radical with a straight or branched chain containing up to 7 carbon atoms in the main chain, which is unsubstituted or substituted with hydroxyl groups and which can comprise, in addition to oxygen, nitrogen and sulfur atoms, 1 to 3 aromatic and/or heterocyclic rings; the oxygen, nitrogen and sulfur atoms being present in the form of ether, thioether, sulfoxide, sulfone, sulfonium, alkylamine or alkenylamine groups, hydroxyl, benzylamine, amine oxide, quaternary ammonium, amide, imide, alcohol, ester and/or urethane groups;

b) polymers of formula:

-D-X-D-X-D- (XIII)

where D denotes a radical

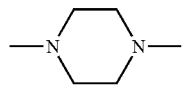

and X denotes the symbol E or E' and at least once E'; E having the meaning given above and E' is a divalent radical that is an alkylene radical with a straight or branched chain having up to 7 carbon atoms in the main chain, which is unsubstituted or substituted with one or more hydroxyl radicals and containing one or more nitrogen atoms, the nitrogen atom being substituted with an alkyl chain that is optionally interrupted by an oxygen atom and necessarily comprising one or more carboxyl functions or one or more hydroxyl functions and betainized by reaction with chloroacetic acid or sodium chloroacetate.

(9) ($C_1$-$C_\infty$)Alkyl vinyl ether/maleic anhydride copolymers partially modified by semiamidation with an N,N-dialkylaminoalkylamine such as N,N-dimethylaminopropylamine or by semiesterification with an N,N-dialkanolamine. These copolymers can also comprise other vinyl comonomers such as vinylcaprolactam.

The amphoteric polymers that are particularly preferred according to the invention are those of family (1).

The silicones that may be used in accordance with the invention are in particular polyorganosiloxanes that are insoluble in the composition and may be in the form of oils, waxes, resins or gums.

Organopolysiloxanes are defined in greater detail in Walter Noll's *Chemistry and Technology of Silicones* (1968), Academic Press. They can be volatile or non-volatile.

When they are volatile, the silicones are more particularly chosen from those with a boiling point of between 60° C. and 260° C., and even more particularly from: (i) cyclic silicones comprising from 3 to 7 and preferably 4 to 5 silicon atoms. These are, for example, octamethylcyclotetrasiloxane sold especially under the name Volatile Silicone 7207 by Union Carbide or Silbione 70045 V 2 by Rhodia Chimie, decamethylcyclopentasiloxane sold under the name Volatile Silicone 7158 by Union Carbide, and Silbione 70045 V 5 by Rhodia Chimie, and mixtures thereof. Mention may also be made of cyclocopolymers of the dimethylsiloxane/methylalkylsiloxane type, such as Volatile Silicone FZ 3109 sold by the company Union Carbide, of chemical structure:

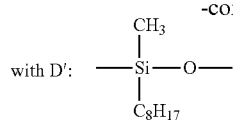

-continued

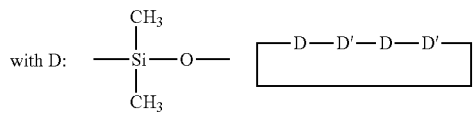

Mention may also be made of mixtures of cyclic silicones with organosilicon compounds, such as the mixture of octamethylcyclotetrasiloxane and tetrakis(trimethylsilyl)pentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones containing 2 to 9 silicon atoms and having a viscosity of less than or equal to $5 \times 10^{-6}$ $m^2$/s at 25° C. An example is decamethyltetrasiloxane sold in particular under the name SH 200 by the company Toray Silicone. Silicones belonging to this category are also described in the article published in Cosmetics and Toiletries, Vol. 91, January 76, pp. 27-32, Todd & Byers, *Volatile Silicone Fluids for Cosmetics*.

Non-volatile silicones and more particularly polyalkylsiloxanes, polyarylsiloxanes, polyalkylarylsiloxanes, silicone gums and resins, and polyorganosiloxanes modified with organofunctional groups, and mixtures thereof, are preferably used.

These silicones are more particularly chosen from polyalkylsiloxanes, among which mention may be made mainly of polydimethylsiloxanes containing trimethylsilyl end groups having a viscosity of from $5 \times 10^{-6}$ to 2.5 $m^2$/s at 25° C. and preferably $1 \times 10^{-5}$ to 1 $m^2$/s. The viscosity of the silicones is measured, for example, at 25° C. according to standard ASTM 445 Appendix C.

Among these polyalkylsiloxanes, mention may be made, in a non-limiting manner, of the following commercial products:

the Silbione oils of the 47 and 70 047 series or the Mirasil oils sold by Rhodia Chimie, such as, for example, the oil 70 047 V 500 000;

the oils of the Mirasil series sold by the company Rhodia Chimie;

the oils of the 200 series from the company Dow Corning, such as, more particularly, DC200 with a viscosity of 60 000 cSt;

the Viscasil oils from General Electric and certain oils of the SF series (SF 96, SF 18) from General Electric.

Mention may also be made of polydimethylsiloxanes with dimethylsilanol end groups (dimethiconol according to the CTFA name), such as the oils of the 48 series from the company Rhodia Chimie.

In this category of polyalkylsiloxanes, mention may also be made of the products sold under the names Abil Wax 9800 and 9801 by the company Goldschmidt, which are poly($C_1$-$C_{20}$)alkylsiloxanes.

The polyalkylarylsiloxanes are particularly chosen from linear and/or branched polydimethyl methylphenylsiloxanes and polydimethyl diphenylsiloxanes with a viscosity of from $1 \times 10^{-5}$ to $5 \times 10^{-2}$ $m^2$/s at 25° C.

Mention may be made, among these polyalkylarylsiloxanes, by way of example, of the products sold under the following names:

the Silbione oils of the 70 641 series from Rhodia Chimie;
the oils of the Rhodorsil 70 633 and 763 series from Rhodia Chimie;
the oil Dow Corning 556 Cosmetic Grade Fluid from Dow Corning;

the silicones of the PK series from Bayer, such as the product PK20;
the silicones of the PN and PH series from Bayer, such as the products PN1000 and PH1000;
certain oils of the SF series from General Electric, such as SF 1023, SF 1154, SF 1250 and SF 1265.

The silicone gums that may be used in accordance with the invention are especially polydiorganosiloxanes having high number-average molecular masses of between 200 000 and 1 000 000, used alone or as a mixture in a solvent. This solvent may be chosen from volatile silicones, polydimethylsiloxane (PDMS) oils, polyphenylmethylsiloxane (PPMS) oils, isoparaffins, polyisobutylenes, methylene chloride, pentane, dodecane and tridecane, or mixtures thereof.

Mention may be made more particularly of the following products:
polydimethylsiloxane,
polydimethylsiloxane/methylvinylsiloxane gums,
polydimethylsiloxane/diphenylsiloxane,
polydimethylsiloxane/phenylmethylsiloxane,
polydimethylsiloxane/diphenylsiloxane/methylvinylsiloxane.

Products that may be used more particularly in accordance with the invention are mixtures, such as:
mixtures formed from a polydimethylsiloxane hydroxylated at the end of the chain (known as dimethiconol according to the nomenclature of the CTFA dictionary) and from a cyclic polydimethylsiloxane (known as cyclomethicone according to the nomenclature of the CTFA dictionary), such as the product Q2 1401 sold by the company Dow Corning;
mixtures formed from a polydimethylsiloxane gum with a cyclic silicone, such as the product SF 1214 Silicone Fluid from the company General Electric, this product being an SF 30 gum corresponding to a dimethicone, having a number-average molecular weight of 500 000, dissolved in the oil SF 1202 Silicone Fluid corresponding to decamethylcyclopentasiloxane;
mixtures of two PDMSs of different viscosities, and more particularly of a PDMS gum and a PDMS oil, such as the product SF 1236 from General Electric. The product SF 1236 is a mixture of a gum SE 30 defined above, with a viscosity of 20 $m^2/s$ and of an oil SF 96 with a viscosity of $5 \times 10^{-6}$ $m^2/s$. This product preferably comprises 15% of gum SE 30 and 85% of an oil SF 96.

The organopolysiloxane resins that may be used in accordance with the invention are crosslinked siloxane systems containing the following units:
$R_2SiO_{2/2}$, $R_3SiO_{1/2}$, $RSiO_{3/2}$ and $SiO_{4/2}$ in which R represents a hydrocarbon group containing 1 to 16 carbon atoms or a phenyl group. Among these products, those particularly preferred are the ones in which R denotes a $C_1$-$C_4$ lower alkyl radical, more particularly methyl, or a phenyl radical.

Mention may be made, among these resins, of the product sold under the name Dow Corning 593 or those sold under the names Silicone Fluid SS 4230 and SS 4267 by General Electric, which are silicones of dimethyl/trimethylsiloxane structure.

Mention may also be made of the resins of the trimethylsiloxysilicate type, sold in particular under the names X22-4914, X21-5034 and X21-5037 by Shin-Etsu.

The organomodified silicones that may be used in accordance with the invention are silicones as defined previously and comprising in their structure one or more organofunctional groups attached via a hydrocarbon-based radical.

Mention may be made, among the organomodified silicones, of polyorganosiloxanes comprising:

polyethylenoxy and/or polypropylenoxy groups optionally comprising $C_6$-$C_{24}$ alkyl groups such as the products known as dimethicone copolyol sold by the company Dow Corning under the name DC1248 or the oils Silwet L722, L7500, L77 and L711 by the company Union Carbide and the $(C_{12})$alkyl methicone copolyol sold by the company Dow Corning under the name Q2 5200;
substituted or unsubstituted amine groups such as the products sold under the name GP 4 Silicone Fluid and GP 7100 by the company Genesee or the products sold under the names Q2 8200 and Dow Corning 929 or 939 by the company Dow Corning. The substituted amine groups are, in particular, $C_1$-$C_4$ aminoalkyl groups;
thiol groups, such as the products sold under the names GP 72 A and GP 71 from Genesee;
alkoxylated groups, such as the product sold under the name Silicone Copolymer F755 by SWS Silicones and Abil Wax 2428, 2434 and 2440 by the company Goldschmidt;
hydroxylated groups, such as the polyorganosiloxanes containing a hydroxyalkyl function, described in French patent application FR-A-85/16334 corresponding to formula (XIV):

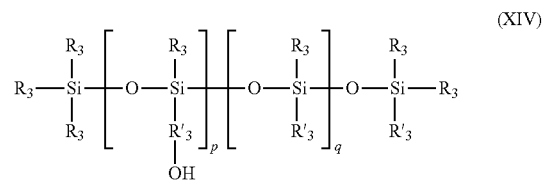

(XIV)

in which the radicals $R_3$, which may be identical or different, are chosen from methyl and phenyl radicals; at least 60 mol % of the radicals $R_3$ denoting methyl; the radical $R'_3$ is a divalent $C_2$-$C_{18}$ hydrocarbon-based alkylene chain unit; p is between 1 and 30 inclusive; q is between 1 and 150 inclusive;
acyloxyalkyl groups, for instance the polyorganosiloxanes described in U.S. Pat. No. 4,957,732 and corresponding to formula (XV);

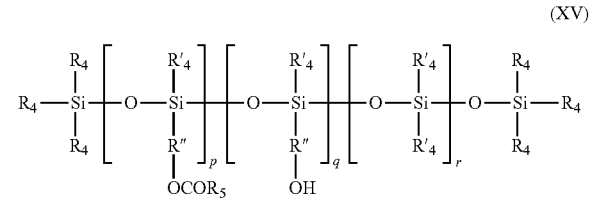

(XV)

in which:
$R_4$ denotes a methyl, phenyl, $OCOR_5$ or hydroxyl group, but only one of the radicals $R_4$ per silicon atom may be OH;
$R'_4$ denotes methyl or phenyl, at least 60 mol % of all the radicals $R_4$ and $R'_4$ denoting methyl;
$R_5$ denotes $C_8$-$C_{20}$ alkyl or alkenyl;
R" denotes a linear or branched, divalent $C_2$-$C_{18}$ hydrocarbon alkylene radical;
r is between 1 and 120 inclusive;
q is between 1 and 30;
q is equal to 0 or is less than 0.5 p, p+q being between 1 and 30; the polyorganosiloxanes of formula (XV) may contain groups:

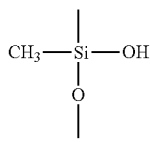

in proportions not exceeding 15% of the sum p+q+r;

anionic groups of the carboxylic type, for instance in the products described in patent EP 186 507 from the company Chisso Corporation, or of the alkylcarboxylic type, such as those present in the product X-22-3701E from the company Shin-Etsu; 2-hydroxyalkyl sulfonate; 2-hydroxyalkyl thiosulfate such as the products sold by the company Goldschmidt under the names Abil S201 and Abil S255;

hydroxyacylamino groups, for instance the polyorganosiloxanes described in patent application EP 342 834. Mention may be made, for example, of the product Q2-8413 from the company Dow Corning.

According to the invention, it is also possible to use silicones comprising a polysiloxane portion and a portion composed of a non-silicone organic chain, with one of the two portions making up the main chain of the polymer and the other being grafted onto said main chain. These polymers are described, for example, in patent applications EP-A-412 704, EP-A-412 707, EP-A-640 105 and WO 95/00578, EP-A-582 152 and WO 93/23009 and U.S. Pat. Nos. 4,693,935, 4,728, 571 and 4,972,037. These polymers are preferably anionic or nonionic.

Such polymers are, for example, copolymers that may be obtained by free-radical polymerization from the monomer mixture formed from:
a) 50% to 90% by weight of tert-butyl acrylate;
b) 0 to 40% by weight of acrylic acid;
c) 5% to 40% by weight of a silicone macromer of formula:

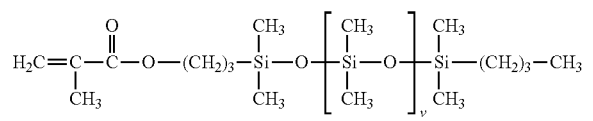
(XVI)

where v is a number ranging from 5 to 700; the weight percentages being calculated relative to the total weight of the monomers.

Other examples of grafted silicone polymers are especially polydimethylsiloxanes (PDMS) onto which are grafted, via a connecting unit of thiopropylene type, mixed polymer units of the poly(meth)acrylic acid type and of the polyalkyl (meth) acrylate type and polydimethylsiloxanes (PDMS) onto which are grafted, via a connecting unit of thiopropylene type, polymer units of the polyisobutyl (meth)acrylate type.

According to the invention, all the silicones may also be used in the form of emulsions, nanoemulsions or microemulsions.

The polyorganosiloxanes that are particularly preferred in accordance with the invention are:

non-volatile silicones chosen from the family of polyalkylsiloxanes with trimethylsilyl end groups, such as oils having a viscosity of between 0.2 and 2.5 m²/s at 25° C., for instance the oils of the DC200 series from Dow Corning, in particular the one with a viscosity of 60 000 cSt, or of the Silbione 70047 and 47 series, and more particularly the oil 70 047 V 500 000 sold by the company Rhodia Chimie, and polyalkylsiloxanes with dimethylsilanol end groups, such as dimethiconols, or polyalkylarylsiloxanes, for instance the oil Silbione 70641 V 200 sold by the company Rhodia Chimie;

the organopolysiloxane resin sold under the name Dow Corning 593;

polysiloxanes containing amine groups such as amodimethicones or trimethylsilyl amodimethicones;

The cationic proteins or protein hydrolysates are, in particular, chemically modified polypeptides bearing quaternary ammonium groups at the end of the chain or grafted onto the said chain. Their molecular mass may vary, for example, from 1500 to 10 000 and in particular from 2000 to 5000 approximately. Among these compounds, mention may in particular be made of:

collagen hydrolysates bearing triethylammonium groups, such as the products sold under the name Quat-Pro E by the company Maybrook and referred to in the CTFA dictionary as Triethonium Hydrolyzed Collagen Ethosulfate;

collagen hydrolysates bearing trimethylammonium chloride and trimethylstearylammonium chloride groups, which are sold under the name Quat-Pro S by the company Maybrook and are referred to in the CTFA dictionary as Steartrimonium Hydrolyzed Collagen;

animal protein hydrolysates bearing trimethylbenzylammonium groups, such as the products sold under the name Crotein BTA by the company Croda and referred to in the CTFA dictionary as Benzyltrimonium hydrolyzed animal protein;

protein hydrolysates bearing, on the polypeptide chain, quaternary ammonium groups comprising at least one alkyl radical containing from 1 to 18 carbon atoms.

Among these protein hydrolysates, mention may be made, inter alia, of:

Croquat L, in which the quaternary ammonium groups comprise a $C_{12}$ alkyl group;

Croquat M, in which the quaternary ammonium groups comprise $C_{10}$-$C_{18}$ alkyl groups;

Croquat S, in which the quaternary ammonium groups comprise a $C_{18}$ alkyl group;

Crotein Q, in which the quaternary ammonium groups comprise at least one alkyl group containing from 1 to 18 carbon atoms.

These various products are sold by the company Croda.

Other quaternized proteins or hydrolysates are, for example, those corresponding to the formula (XVII):

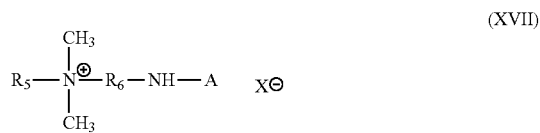
(XVII)

in which X⁻ is an anion of an organic or inorganic acid, A denotes a protein residue derived from collagen protein hydrolysates, $R_5$ denotes a lipophilic group comprising up to 30 carbon atoms, $R_6$ represents an alkylene group containing 1 to 6 carbon atoms. Mention may be made, for example, of the products sold by the company Inolex, under the name Lexein QX 3000, referred to in the CTFA dictionary as Cocotrimonium Collagen Hydrolysate.

Mention may also be made of quaternized plant proteins such as wheat, corn or soybean proteins: quaternized wheat proteins that may be mentioned include those sold by the company Croda under the names Hydrotriticum WQ or QM, which in the CTFA dictionary are called Cocodimonium hydrolyzed wheat protein, or Hydrotriticum QL, which in the CTFA dictionary is called Laurdimonium hydrolyzed wheat protein, or else Hydrotriticum QS, which in the CTFA dictionary is called Steardimonium hydrolyzed wheat protein.

According to the present invention, the compounds of ceramide type are especially natural or synthetic ceramides and/or glycoceramides and/or pseudoceramides and/or neoceramides.

Compounds of ceramide type are described, for example, in patent applications DE4424530, DE4424533, DE4402929, DE4420736, WO95/23807, WO94/07844, EP-A-0646572, WO95/16665, FR-2 673 179, EP-A-0227994 and WO 94/07844, WO94/24097, WO94/10131, the teachings of which are included herein by way of reference.

Compounds of ceramide type that are particularly preferred according to the invention are, for example:

2-N-linoleoylaminooctadecane-1,3-diol,
2-N-oleoylaminooctadecane-1,3-diol,
2-N-palmitoylaminooctadecane-1,3-diol,
2-N-stearoylaminooctadecane-1,3-diol,
2-N-behenoylaminooctadecane-1,3-diol,
2-N-[2-hydroxypalmitoyl]aminooctadecane-1,3-diol,
2-N-stearoylaminooctadecane-1,3,4-triol and in particular N-stearoylphytosphingosine,
2-N-palmitoylaminohexadecane-1,3-diol,
bis(N-hydroxyethyl-N-cetyl)malonamide,
cetylic acid N-(2-hydroxyethyl)-N-(3-cetyloxy-2-hydroxypropyl)amide,
N-docosanoyl-N-methyl-D-glucamine,
or mixtures of these compounds.

Cationic surfactants may also be used, among which mention may be made in particular of: salts of optionally polyoxyalkylenated primary, secondary or tertiary fatty amines; quaternary ammonium salts; imidazoline derivatives; or amine oxides of cationic nature.

Examples of quaternary ammonium salts include:
those of general formula (XVIII) below:

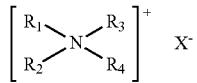

(XVIII)

in which the radicals $R_1$ to $R_4$, which can be identical or different, represent a linear or branched aliphatic radical comprising from 1 to 30 carbon atoms or an aromatic radical, such as aryl or alkylaryl. The aliphatic radicals may contain heteroatoms such as, in particular, oxygen, nitrogen, sulfur and halogens. The aliphatic radicals are chosen, for example, from alkyl, alkoxy, polyoxy($C_2$-$C_6$)alkylene, alkylamide, ($C_{12}$-$C_{22}$)-alkylamido($C_2$-$C_6$)alkyl, ($C_{12}$-$C_{22}$)alkylacetate and hydroxyalkyl radicals, comprising from about 1 to 30 carbon atoms; X is an anion chosen from the group of halides, phosphates, acetates, lactates, ($C_2$-$C_6$)alkyl sulfates and alkyl or alkylaryl sulfonates. Preferably, R1 and R2 denote $C_1$-$C_4$ alkyl or $C_1$-$C_4$ hydroxyalkyl.

Among the quaternary ammonium salts of formula (XVIII), preference is given firstly to tetraalkylammonium chlorides, for instance dialkyldimethylammonium or alkyltrimethylammonium chlorides in which the alkyl radical contains approximately from 12 to 22 carbon atoms, in particular behenyltrimethylammonium chloride, distearyldimethylammonium chloride, cetyltrimethylammonium chloride, benzyldimethylstearylammonium chloride, or else, secondly, palmitylamidopropyltrimethylammonium chloride or stearamidopropyldimethyl(myristyl acetate)ammonium chloride;

quaternary ammonium salts of imidazolinium, for instance the salt of formula (XIX) below:

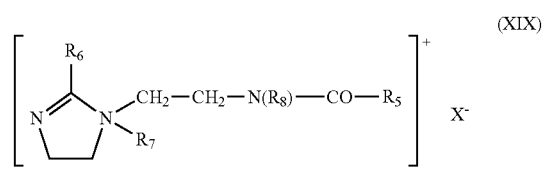

(XIX)

in which $R_5$ represents an alkenyl or alkyl radical containing from 8 to 30 carbon atoms, for example coconut fatty acid derivatives, $R_6$ represents a hydrogen atom, a $C_1$-$C_4$ alkyl radical or an alkenyl or alkyl radical containing from 8 to 30 carbon atoms, $R_7$ represents a $C_1$-$C_4$ alkyl radical, $R_8$ represents a hydrogen atom or a $C_1$-$C_4$ alkyl radical, X is an anion chosen from the group of halides, phosphates, acetates, lactates, alkyl sulfates and alkyl or alkylaryl sulfonates. $R_5$ and $R_6$ preferably denote a mixture of alkenyl or alkyl radicals containing from 12 to 21 carbon atoms, for example tallow fatty acid derivatives, $R_7$ denotes a methyl radical and $R_8$ denotes a hydrogen atom. Such a product is sold, for example, under the name Rewoquat W 75 by the company Degussa;

the diquaternary ammonium salts of formula (XX):

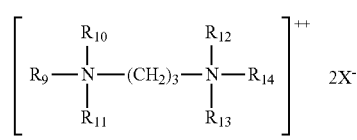

(XX)

in which $R_9$ denotes an aliphatic radical containing from about 16 to 30 carbon atoms, $R_{10}$, $R_{11}$, $R_{12}$, $R_{13}$ and $R_{14}$, which may be identical or different, are chosen from hydrogen or an alkyl radical containing from 1 to 4 carbon atoms, and X is an anion chosen from the group of halides, acetates, phosphates, nitrates and methyl sulfates. Such diquaternary ammonium salts in particular comprise propanetallowediammonium dichloride;

quaternary ammonium salts containing at least one ester function.

The quaternary ammonium salts containing at least one ester function that may be used according to the invention are, for example, those of formula (XXI) below:

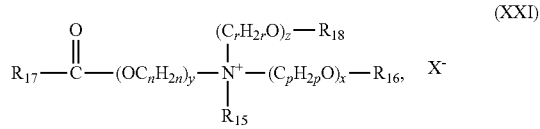

(XXI)

in which:

R15 is selected from $C_1$-$C_6$ alkyl radicals and $C_1$-$C_6$ hydroxyalkyl or dihydroxyalkyl radicals;

R16 is selected from:
the radical

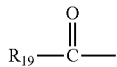

linear or branched, saturated or unsaturated $C_1$-$C_{22}$ hydrocarbon-based radicals R20,
a hydrogen atom,
R18 is selected from:
the radical

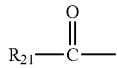

linear or branched, saturated or unsaturated $C_1$-$C_6$ hydrocarbon radicals R22,
a hydrogen atom,
R17, R19 and R21, which are identical or different, are selected from linear or branched, saturated or unsaturated $C_7$-$C_{21}$ hydrocarbon radicals;
n, p and r, which may be identical or different, are integers ranging from 2 to 6;
y is an integer ranging from 1 to 10;
x and z, which may be identical or different, are integers ranging from 0 to 10;
$X^-$ is a simple or complex, organic or inorganic anion;
with the proviso that the sum x+y+z is from 1 to 15, that when x is 0, then R16 denotes R20 and that when z is 0, then R18 denotes R22.

The alkyl radicals R15 may be linear or branched, and more particularly linear.

Preferably R15 denotes a methyl, ethyl, hydroxyethyl or dihydroxypropyl radical, and more particularly a methyl or ethyl radical.

Advantageously, the sum x+y+z is from 1 to 10.

When R16 is a hydrocarbon radical R20, it may be long and may have 12 to 22 carbon atoms, or may be short and may have from 1 to 3 carbon atoms.

When R18 is a hydrocarbon radical R22, it has preferably 1 to 3 carbon atoms.

Advantageously, R17, R19 and R21, which may be identical or different, are chosen from linear or branched, saturated or unsaturated $C_{11}$-$C_{21}$ hydrocarbon-based radicals, and more particularly from linear or branched, saturated or unsaturated $C_{11}$-$C_{21}$ alkyl and alkenyl radicals.

Preferably, x and z, which may be identical or different, are equal to 0 or 1.

Advantageously, y is equal to 1.

Preferably n, p and r, which may be identical or different, are equal to 2 or 3, and more particularly are equal to 2.

The anion is preferably a halide (chloride, bromide or iodide) or an alkyl sulfate, more particularly methyl sulfate. However, it is possible to use methanesulfonate, phosphate, nitrate, tosylate, an anion derived from an organic acid, such as acetate or lactate, or any other anion that is compatible with the ammonium containing an ester function.

The anion $X^-$ is even more particularly chloride or methyl sulfate.

The ammonium salts more particularly used are those of formula (XXI) in which:
R15 denotes a methyl or ethyl radical;
x and y are equal to 1;
z is equal to 00 or 1;
n, p and r are equal to 2;
R16 is chosen from:
the radical

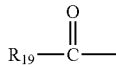

methyl, ethyl or $C_{14}$-$C_{22}$ hydrocarbon-based radicals,
a hydrogen atom;
R18 is chosen from:
the radical

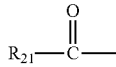

a hydrogen atom.
R17, R19 and R21, which may be identical or different, are chosen from linear or branched, saturated or unsaturated $C_{13}$-$C_{17}$ hydrocarbon-based radicals, and preferably from linear or branched, saturated or unsaturated $C_{13}$-$C_{17}$ alkyl and alkenyl radicals.

The hydrocarbon-based radicals are advantageously linear.

Examples of compounds of formula (XXI) that may be mentioned include the diacyloxyethyldimethylammonium, diacyloxyethylhydroxyethylmethylammonium, monoacyloxyethyldihydroxyethylmethylammonium, triacyloxyethylmethylammonium and monoacyloxyethylhydroxyethyldimethylammonium salts (chloride or methyl sulfate in particular), and mixtures thereof. The acyl radicals preferably contain 14 to 18 carbon atoms and are obtained more particularly from a plant oil such as palm oil or sunflower oil. When the compound contains several acyl radicals, these radicals may be identical or different.

These products are obtained, for example, by direct esterification of triethanolamine, triisopropanolamine, an alkyldiethanolamine or an alkyldiisopropanolamine, which are optionally oxyalkylenated, with fatty acids or with fatty acid mixtures of plant or animal origin, or by transesterification of the methyl esters thereof. This esterification is followed by a quaternization using an alkylating agent such as an alkyl halide (preferably a methyl or ethyl halide), a dialkyl sulfate (preferably dimethyl or diethyl sulfate), methyl methanesulfonate, methyl para-toluenesulfonate, glycol chlorohydrin or glycerol chlorohydrin.

Such compounds are sold, for example, under the names Dehyquart by the company Cognis, Stepanquat by the company Stepan, Noxamium by the company CECA or Rewoquat WE 18 by the company Degussa.

It is also possible to use the ammonium salts containing at least one ester function that are described in U.S. Pat. Nos. 4,874,554 and 4,137,180.

Among the quaternary ammonium salts of formula (XXIV) that are preferred are, on the one hand, tetraalkylammonium chlorides, for instance dialkyldimethylammonium or alkyltrimethylammonium chlorides in which the alkyl radical contains from about 12 to 22 carbon atoms, in particular behenyltrimethylammonium chloride, distearyldimethylammonium chloride, cetyltrimethylammonium chloride or benzyldimethylstearylammonium chloride, or, on the other hand, stearamidopropyldimethyl(myristyl acetate)ammonium chloride sold under the name Ceraphyl 70 by the company Van Dyk.

It is, of course, possible to use mixtures of conditioning agents.

Preferably, the conditioning agent(s) according to the invention are chosen from fatty substances, cationic polymers, cationic surfactants, and mixtures of these compounds.

According to the invention, the conditioning agent(s) may represent from 0.001% to 99% by weight, preferably from 0.01% to 95% by weight, more particularly from 0.1% to 95% by weight and better still from 0.2% to 20% by weight, relative to the total weight of the composition.

The composition according to the invention may be used in the presence of one or more catalysts to catalyse the hydrolysis-condensation reactions of the alkoxysilane functions of the polymer of formula (I) according to the invention.

The catalyst may be chosen from acids and bases.

The acid may be chosen from mineral acids and organic acids.

The acid may be chosen in particular from lactic acid, acetic acid, citric acid, tartaric acid, hydrochloric acid, sulfuric acid and phosphoric acid, preferably hydrochloric acid.

The base may be chosen from mineral bases and organic bases.

The base may be chosen from ammonia and sodium hydroxide.

The catalyst may also be chosen from alkoxysilane monomers, optionally bearing an amine function, for instance aminopropyltriethoxysilane or octyltriethoxysilane.

The catalyst may be present in the composition according to the invention, or it may be mixed at the time of use with the composition according to the invention, or alternatively it may be applied sequentially to the keratin fibres before or after the composition according to the invention.

When they are present in the composition according to the invention, the catalyst(s) may represent from 0.0001% to 10% by weight, preferably from 0.001% to 5% by weight and more particularly from 0.01% to 2% by weight relative to the total weight of the composition.

The composition of the invention may be aqueous or anhydrous. If the composition is aqueous, it preferably comprises from 5% to 99% by weight of water, better still from 20% to 95% by weight of water, even better still from 50% to 95% by weight of water relative to the total weight of the composition.

The composition according to the invention may also comprise one or more organic solvents such as linear or branched $C_2$-$C_4$ alkanols, for instance ethanol, polyols, glycol ethers or aromatic alcohols.

If they are present, the organic solvents may then represent from 1% to 99%, preferably from 5% to 99% by weight and better still from 10% to 40% by weight relative to the total weight of the composition.

The composition is preferably aqueous.

The composition may be in the form of a solution, a dispersion or an emulsion.

The polymer may be emulsified as an oil-in-water or water-in-oil emulsion or as a multiple emulsion.

The composition according to the invention may also contain one or more additives chosen from nonionic, anionic and amphoteric surfactants, vitamins and provitamins including panthenol, water-soluble and liposoluble sunscreens, fillers and solid particles, for instance mineral and organic, coloured or uncoloured pigments, nacreous agents and opacifiers, glitter flakes, active particles, mineral fillers, dyes, sequestrants, plasticizers, solubilizers, acidifying agents, basifying agents, neutralizers, mineral and organic thickeners, antioxidants, antifoams, moisturizers, emollients, hydroxy acids, penetrants, fragrances and preserving agents.

Needless to say, a person skilled in the art will take care to select the optional additional compounds and/or the amount thereof such that the advantageous properties of the compositions used according to the invention are not, or are not substantially, adversely affected by the envisaged addition.

The composition of the invention may be in the form of a foam, a gel, a serum, a cream, a paste, a wax, a liquid lotion or a lacquer.

The composition may be packaged in a pump-dispenser bottle or in an aerosol device.

When it is packaged in an aerosol-type device, the liquid phase/propellant weight ratio of the pressurized composition of the present invention is preferably between 50 and 0.05, and in particular between 50 and 1.

For the aerosol formulations, the composition preferably comprises one or more solvents chosen from water, $C_1$-$C_4$ alcohols such as ethanol, isopropanol, tert-butanol or n-butanol; propylene carbonate, polyols such as propylene glycol and polyol ethers; acetone, and mixtures thereof, the preferred solvent being ethanol.

Preferably, the composition is aqueous or aqueous-alcoholic, the alcohol being a $C_1$-$C_4$ alcohol.

When the alcohol is present, its proportion is especially between 1% and 99% by weight, preferably between 5% and 80% by weight and even more preferentially between 8% and 50% by weight relative to the total weight of the hair treatment composition and of the propellant.

For the aerosol formulations, any liquefiable gas customarily used in aerosol devices will be used as propellant gas. Use will be made especially of dimethyl ether, $C_3$-$C_5$ alkanes, chlorinated and/or fluorinated, halogenated or non-halogenated, volatile hydrocarbons, usually used in aerosol devices. Carbon dioxide, nitrous oxide, nitrogen or compressed air, or mixtures thereof, may also be used as propellant.

Preferably, the compound(s) constituting the propellant gas used are chosen from non-halogenated $C_3$-$C_5$ alkanes, such as propane, n-butane and isobutane, halogenated, and in particular chlorinated and/or fluorinated, $C_3$-$C_5$ alkanes, such as 1,1-difluoroethane, and mixtures thereof.

According to a particularly preferred embodiment, the alkane(s) of the propellant gas are non-halogenated. Even more preferentially, the propellant gas is dimethyl ether or a mixture of propane, n-butane and isobutane.

In the case of aerosol foams, the composition introduced into the aerosol device may, for example, be in the form of a lotion, or dispersions or emulsions which, after dispensing from the aerosol device, form foams to be applied to keratin substances.

These foams must be sufficiently stable not to rapidly liquefy and must also rapidly disappear, either spontaneously or during the massaging which is used to cause the composition to penetrate into keratin substances and/or to distribute the composition over keratin substances and more particularly the head of hair and/or the hair.

In the case of aerosol foams, the composition according to the invention may also contain at least one cationic, nonionic, anionic or amphoteric surfactant.

The propellant gas is present in the composition according to the invention in proportions preferably ranging from 1% to 99% by weight, more preferentially from 1.5% to 50% by weight and better still from 2% to 30% by weight, relative to the total weight of the composition.

The aerosol device used to package the composition of the invention may be made up of two compartments, formed from an outer aerosol can comprising an inner bag hermetically sealed to a valve. The composition is introduced into the inner bag and a compressed gas is introduced between the bag and the can at a pressure sufficient to make the product come out in the form of a spray through a nozzle orifice. Such a device is sold, for example, under the name EP Spray by the company EP-Spray System SA. The said compressed gas is preferably used at a pressure of between 1 and 12 bar and even better still between 9 and 11 bar.

The invention also relates to a cosmetic process for treating keratin fibres such as the hair, which consists in applying thereto a composition as defined previously, and optionally in applying one or more catalysts as defined previously, the catalyst(s) possibly being applied before, after or at the same time as the composition.

The composition is applied to wet or dry hair.

According to the desired type of hairstyle, it is applied in combination with a heating tool or at room temperature.

The heating tool may be a straightening iron, a curling iron, a crimping iron, a waving iron, a hood or a hairdryer.

The composition may or may not, as indicated above, also contain a catalyst that may be chosen from acids, bases and alkoxysilanes. In the latter case, aminopropyltriethoxysilane will be preferred.

According to one particular embodiment, the application may be made in a single stage. In this case, a composition simultaneously containing one or more polymers of formula (I), one or more conditioning agents and optionally one or more catalysts as defined previously will be applied.

In this one-stage embodiment, the composition applied to the keratin fibres may result from the mixing of a composition comprising one or more polymers of formula (I) and one or more conditioning agents and a composition comprising one or more catalysts as defined previously.

According to another embodiment, the application may be performed in two stages: in a first step (A), the composition comprising one or more catalysts as defined previously is applied, and in a second step (B), the composition comprising one or more polymers of formula (I) and one or more conditioning agents is applied; in this embodiment, step (A) and then step (B) may be performed, or alternatively step (B) and then step (A), with or without intermediate drying. Preferably, step (A) and then step (B) is performed. In this particular embodiment, intermediate drying is preferably performed.

The invention also relates to a multi-compartment device comprising:
- a first compartment containing a composition comprising one or more polymers of formula (I) and one or more conditioning agents;
- a second compartment containing a composition comprising one or more catalysts as defined previously.

The device according to the invention may be intended for application in one stage or in two stages.

In the case of a one-stage application, the compositions of the first and second compartments may be dispensed simultaneously at the time of application.

Finally, the present invention relates to the use of a composition comprising one or more polymers of formula (I) and one or more conditioning agents for treating keratin fibres, especially the hair, and in particular for shaping the hair.

The invention is illustrated in more detail in the following examples, which are provided by way of illustration and without limitation of the invention.

EXAMPLES

The following compositions were prepared, the contents being expressed on a weight basis relative to the total weight of the composition:

| Examples | Polymer of formula (I)* | Octyldodecanol | Ethanol |
|---|---|---|---|
| Example 1 | 30 | 0.5 | qs 100 |
| Example 2 | 10 | 0.5 | qs 100 |
| Example 3 | 5 | 0.5 | qs 100 |
| Control 1 | 0 | 0.5 | qs 100 |

*Geniosil STP-E10 sold by Wacker

| Examples | Polymer of formula (I)* | Caprylic/capric triglyceride** |
|---|---|---|
| Example 4 | 5 | 95 |
| Control 2 | 0 | 100 |

*Geniosil STP-E10 sold by Wacker
**Myritol 318 sold by Cognis

| Examples | Polymer of formula (I)* | Guar hydroxypropyl trimonium chloride | Ethanol | Water |
|---|---|---|---|---|
| Example 5 | 5 | 0.1 | qs 100 | 20 |
| Control 3 | 0 | 0.1 | qs 100 | 20 |

*Geniosil STP-E10 sold by Wacker

| Example | Polymer of formula (I)* | Guar hydroxypropyl trimonium chloride | Ethanol | Water | Lotion 1 |
|---|---|---|---|---|---|
| Example 6 | 5 | 0.1 | 75 | 19 | 1 |

*Geniosil STP-E10 sold by Wacker

| Example | Aminopropyltriethoxysilane | Lactic acid | Water |
|---|---|---|---|
| Lotion 1 | 10 | qs pH = 10 | qs 100 |

| Example | Polymer of formula (I)* | Hexadimethrine chloride | Ethanol | Water | 0.1N NaOH solution |
|---|---|---|---|---|---|
| Example 7 | 5 | 0.2 AM | 75 | qs 100 | 1 |

*Geniosil STP-E10 sold by Wacker

| Example | Polymer of formula (I)* | Cetrimonium chloride | Ethanol | Water | 0.1N HCl solution |
|---|---|---|---|---|---|
| Example 8 | 5 | 0.2 AM | 75 | qs 100 | 1 |

*Geniosil STP-E10 sold by Wacker

| Examples | Polymer of formula (I)* | Octyldodecanol | Ethanol | Dimethyl ether |
|---|---|---|---|---|
| Example 9 | 3 | 0.5 | 57 | 40 |

*Geniosil STP-E10 sold by Wacker

The composition according to Example 6 will be prepared just before performing the application.
Various modes of application are envisaged:

1) One-Stage Application with a Heating Tool

The compositions according to Examples 1 to 8 are applied to locks of straight chestnut-brown Caucasian hair, with a bath ratio of 0.5.

The lock is then rolled up on a curling iron for 30 seconds.

For comparative purposes, the control compositions 1, 2 and 3 are applied to locks of the same type.

To evaluate the remanence over time, the locks are suspended vertically over a paper and their relaxation is evaluated over time by marking the end of the lock on the paper.

To evaluate the detergent resistance, the locks are placed in a detergent solution at 55° C. for 30 minutes.

The locks obtained with the compositions according to Examples 1 to 8 have a cohesive curl, i.e. the hairs are stuck together within the curl.

The locks obtained with the controls are not cohesive, i.e. the hairs are not stuck together within the curl.

The locks treated with the compositions according to Examples 1 to 5 have very good remanence over time and detergent resistance.

The locks treated with compositions 6 to 8 show even better remanence and also have very good detergent resistance.

The lock treated with the composition according to Example 6 is the one that shows the best remanence.

The locks treated with the control compositions 1 to 3 become relaxed and do not show any detergent resistance.

2) Two-Stage Application with a Heating Tool

The lotion 1 is applied to locks and dried using a hairdryer. The composition according to Examples 1 to 5 is then applied, and the curling iron is then applied for 30 seconds.

To evaluate the remanence over time, the locks are suspended vertically over a paper and their relaxation is evaluated over time by marking the end of the lock on the paper.

To evaluate the detergent resistance, the locks are placed in a detergent solution at 55° C. for 30 minutes.

The locks show very good remanence over time and detergent resistance.

3) Cold Application as a Styling Product

The application is performed in a single stage on malleable heads of short hair.

The composition according to Examples 3 to 8 is applied.

A good styling effect is obtained after drying.

The composition according to Example 6 affords enhanced fixing.

4) Application as an Aerosol

The formulation according to Example 9 is applied to a malleable head of short hair, which allows good fixing.

By successively applying the formulation according to the lotion Example 1 and then the formulation according to Example 9, even greater fixing is obtained.

The invention claimed is:

1. A cosmetic composition comprising:
at least one keratin fiber conditioning agent; and
at least one polymer of formula (I) below:

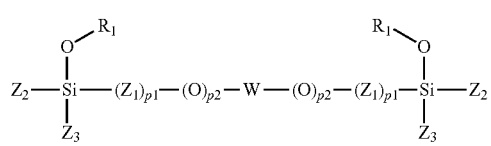

wherein:
$Z_1$ is a divalent group —$CH_2$-T- or -T-$CH_2$—; wherein T is chosen from oxygen, sulfur, and N($R_2$), N($R_2$)—C(O), C(O)—N($R_2$), S—(CO), (CO)—S, O—(CO) and (CO)—O groups;
$Z_2$ is chosen from $OR_1$ and $R_8$—$CH_2$—$NR_3R_4$;
$Z_3$ is chosen from $OR_5$ and $R_6$;
p1 is equal to 1;
p2 is equal to 0 or 1;
$R_2$ and $R_3$, which may be identical or different, are chosen from hydrogen and $R_7$;
$R_1$, $R_5$, $R_6$, $R_7$ and $R_8$, which may be identical or different, are chosen from $C_1$-$C_6$ alkyl groups;
$R_4$ is chosen from $C_1$-$C_6$ alkyl groups and $C_5$-$C_6$ cycloalkyl groups;
$R_3$ and $R_4$ may optionally form, together with the nitrogen atom that bears them, a 5- to 8-membered heterocycle comprising from 1 to 3 heteroatoms; and
W is a divalent polymer chain;
wherein the at least one polymer of formula (I) is present in the cosmetic composition in an amount ranging from about 0.1% to about 40% by weight relative to the total weight of the cosmetic composition.

2. The cosmetic composition according to claim 1, wherein the polymers of formula (I) comprise at least one group chosen from —$CH_2$—N($R_2$)—C(O)—, —C(O)—N($R_2$)—$CH_2$—, and —$CH_2$—$NR_3R_4$.

3. The cosmetic composition according to claim 1, wherein W is a ($C_1$-$C_6$) polyoxyalkylene.

4. The cosmetic composition according to claim 3, wherein W is —(O-ALK)$_n$-, wherein ALK is a $C_1$-$C_6$ alkylene group and n ranges from 5 to 1,000,000.

5. The cosmetic composition according to claim 3, wherein the groups ($C_1$-$C_6$) are chosen from methyl and ethyl groups.

6. The cosmetic composition according to claim 1, wherein the at least one polymer of formula (I) is present in the cosmetic composition in an amount ranging from about 1% to about 10% by weight relative to the total weight of the cosmetic composition.

7. The cosmetic composition according to claim 1, wherein the at least one keratin fiber conditioning agent is chosen from $C_6$-$C_{16}$ hydrocarbons, hydrocarbons containing more than 16 carbon atoms, oils of animal origin, oils of plant origin, glycerides and fluoro oils of synthetic origin, fatty alcohols, fatty acid esters, fatty alcohol esters, non-silicone waxes, silicones, fatty amines, fatty acids, cationic polymers, amphoteric polymers, cationic proteins, cationic protein hydrolysates, compounds of ceramide type, cationic surfactants, and mixtures thereof.

8. The cosmetic composition according to claim 1, wherein the at least one keratin fiber conditioning agent is chosen from fatty substances, cationic polymers, cationic surfactants, silicones, and mixtures thereof.

9. The cosmetic composition according to claim 1, wherein the at least one keratin fiber conditioning agent is present in the cosmetic composition in an amount ranging from about 0.001% to about 99% by weight relative to the total weight of the cosmetic composition.

10. The cosmetic composition according to claim 9, wherein the at least one keratin fiber conditioning agent is present in the cosmetic composition in an amount ranging from about 0.2% to about 20% by weight relative to the total weight of the cosmetic composition.

11. The cosmetic composition according to claim 1, further comprising at least one catalyst.

12. The cosmetic composition according to claim 11, wherein the at least one catalyst is chosen from organic or mineral basic compounds, organic or mineral acids, alkoxysilane monomers, and mixtures thereof.

13. The cosmetic composition according to claim 11, wherein the at least one catalyst is chosen from ammonia, sodium hydroxide, hydrochloric acid, oleic acid, lactic acid, aminopropyltriethoxysilane, and mixtures thereof.

14. The cosmetic composition according to claim 11, wherein the at least one catalyst is present in the cosmetic composition in an amount ranging from about 0.0001% to about 10% by weight relative to the total weight of the cosmetic composition.

15. The cosmetic composition according to claim 14, wherein the at least one catalyst is present in the cosmetic composition in an amount ranging from about 0.1% to about 2% by weight relative to the total weight of the cosmetic composition.

16. A device comprising:
a first compartment containing a composition comprising:
at least one keratin fiber conditioning agent; and
at least one polymer of formula (I) below:

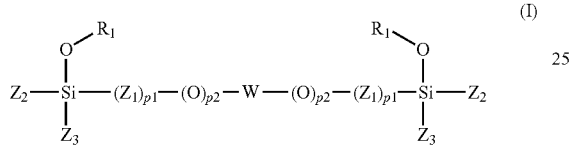

wherein:
$Z_1$ is a divalent group —$CH_2$-T- or -T-$CH_2$—; wherein T is chosen from oxygen, sulfur, and $N(R_2)$, $N(R_2)$—C(O), C(O)—$N(R_2)$, S—(CO), (CO)—S, O—(CO) and (CO)—O groups;
$Z_2$ is chosen from $OR_1$ and $R_8$—$CH_2$—$NR_3R_4$;
$Z_3$ is chosen from $OR_5$ and $R_6$;
p1 is equal to 1;
p2 is equal to 0 or 1;
$R_2$ and $R_3$, which may be identical or different, are chosen from hydrogen and $R_7$;
$R_1$, $R_5$, $R_6$, $R_7$ and $R_8$, which may be identical or different, are chosen from $C_1$-$C_6$ alkyl groups;
$R_4$ is chosen from $C_1$-$C_6$ alkyl groups and $C_5$-$C_6$ cycloalkyl groups;
$R_3$ and $R_4$ may optionally form, together with the nitrogen atom that bears them, a 5- to 8-membered heterocycle comprising from 1 to 3 heteroatoms; and
W is a divalent polymer chain; and
a second compartment containing a composition comprising at least one catalyst chosen from organic or mineral basic compounds, organic or mineral acids, alkoxysilane monomers, and mixtures thereof.

17. A process for the cosmetic treatment of keratin fibers, comprising:
(a) applying to the keratin fibers a cosmetic composition comprising:
at least one keratin fiber conditioning agent; and
at least one polymer of formula (I) below:

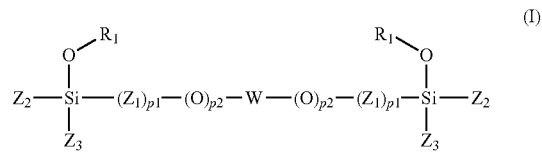

wherein:
$Z_1$ is a divalent group —$CH_2$-T- or -T-$CH_2$—; wherein T is chosen from oxygen, sulfur, and $N(R_2)$, $N(R_2)$—C(O), C(O)—$N(R_2)$, S—(CO), (CO)—S, O—(CO) and (CO)—O groups;
$Z_2$ is chosen from $OR_1$ and $R_8$—$CH_2$—$NR_3R_4$;
$Z_3$ is chosen from $OR_5$ and $R_6$;
p1 is equal to 1;
p2 is equal to 0 or 1;
$R_2$ and $R_3$, which may be identical or different, are chosen from hydrogen and $R_7$;
$R_1$, $R_5$, $R_6$, $R_7$ and $R_8$, which may be identical or different, are chosen from $C_1$-$C_6$ alkyl groups;
$R_4$ is chosen from $C_1$-$C_6$ alkyl groups and $C_5$-$C_6$ cycloalkyl groups;
$R_3$ and $R_4$ may optionally form, together with the nitrogen atom that bears them, a 5- to 8-membered heterocycle comprising from 1 to 3 heteroatoms; and
W is a divalent polymer chain;
and
(b) optionally applying to the keratin fibers at least one catalyst chosen from organic or mineral basic compounds, organic or mineral acids, alkoxysilane monomers, and mixtures thereof,
wherein the at least one catalyst is applied before, after or at the same time as the cosmetic composition.

18. The cosmetic process according to claim 17, further comprising a step of (c) heating the keratin fibers using a heating tool chosen from a straightening iron, a curling iron, a crimping iron, a waving iron, a hood and a hairdryer.

19. The cosmetic process according to claim 17, wherein the keratin fibers are chosen from hair.

20. The cosmetic process according to claim 19, wherein the cosmetic treatment comprises shaping the hair.

* * * * *